US011207165B2

(12) United States Patent
Montpetit et al.

(10) Patent No.: US 11,207,165 B2
(45) Date of Patent: Dec. 28, 2021

(54) SURGICAL ARTICLES AND METHODS FOR TREATING PELVIC CONDITIONS

(71) Applicant: Boston Scientific Scimed, Inc., Maple Grove, MN (US)

(72) Inventors: Karen Pilney Montpetit, Woodbury, MN (US); Kelly Ann Chapman, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 253 days.

(21) Appl. No.: 15/972,824

(22) Filed: May 7, 2018

(65) Prior Publication Data

US 2019/0274804 A1 Sep. 12, 2019

Related U.S. Application Data

(63) Continuation of application No. 12/666,953, filed as application No. PCT/US2008/008006 on Jun. 27, 2008, now Pat. No. 9,974,636.

(60) Provisional application No. 60/947,044, filed on Jun. 29, 2007.

(51) Int. Cl.
*A61F 2/00* (2006.01)
*A61B 17/06* (2006.01)
*A61B 17/00* (2006.01)

(52) U.S. Cl.
CPC ...... *A61F 2/0045* (2013.01); *A61B 17/06109* (2013.01); *A61B 2017/00805* (2013.01)

(58) Field of Classification Search
CPC .... A61F 2/0004; A61F 2/0031; A61F 2/0036; A61F 2/0045; A61F 2/0063; A61F 2/02; A61B 17/0469; A61B 17/06004; A61B 17/06066; A61B 17/06109
See application file for complete search history.

(56) References Cited

U.S. PATENT DOCUMENTS

| 4,741,330 | A  | 5/1988  | Hayhurst        |
| 5,368,602 | A  | 11/1994 | de la Torre     |
| 5,405,360 | A  | 4/1995  | Tovey           |
| 5,647,836 | A  | 7/1997  | Blake, III et al. |
| 6,382,214 | B1 | 5/2002  | Raz et al.      |
| 6,416,486 | B1 | 7/2002  | Wampler         |
| 6,478,727 | B2 | 11/2002 | Scetbon         |
| 6,575,897 | B1 | 6/2003  | Ory et al.      |

(Continued)

FOREIGN PATENT DOCUMENTS

| DE | 202006016866 U1 | 2/2007  |
| EP | 2510903 A2      | 10/2012 |

(Continued)

OTHER PUBLICATIONS

Communication under Rule 71(3) EPC for European Application No. 12175392.5, dated Oct. 9, 2017, 7 pages.

*Primary Examiner* — Samuel G Gilbert
(74) *Attorney, Agent, or Firm* — Brake Hughes Bellermann LLP

(57) ABSTRACT

According to an aspect, pelvic implants optionally including the ability to engage a spreader tool for spreading the implant within the patient, also optionally including a frame, exemplary implants being capable of being used to treat pelvic floor disorders, for example by supporting of levator tissue, and methods of surgically placing pelvic implants.

13 Claims, 13 Drawing Sheets

(56) References Cited

U.S. PATENT DOCUMENTS

| | | |
|---|---|---|
| 6,612,807 B2 | 9/2003 | Czachor et al. |
| 6,641,524 B2 | 11/2003 | Kovac |
| 6,652,450 B2 | 11/2003 | Neisz et al. |
| 6,669,735 B1 | 12/2003 | Pelissier |
| 6,802,807 B2 | 10/2004 | Anderson et al. |
| 6,911,003 B2 | 6/2005 | Anderson et al. |
| 6,971,986 B2 | 12/2005 | Westrum et al. |
| 7,070,556 B2 | 7/2006 | Anderson et al. |
| 7,351,197 B2 | 4/2008 | Montpetit et al. |
| 7,407,480 B2 | 8/2008 | Staskin et al. |
| 7,422,557 B2 | 9/2008 | Rehder et al. |
| 7,500,945 B2 | 3/2009 | Cox et al. |
| 7,828,715 B2 | 11/2010 | Haverfield |
| 7,914,437 B2 | 3/2011 | Rehder et al. |
| 8,097,008 B2 | 1/2012 | Henderson |
| 2002/0161382 A1 | 10/2002 | Neisz et al. |
| 2003/0212305 A1 | 11/2003 | Anderson et al. |
| 2004/0106847 A1 | 6/2004 | Benderev |
| 2005/0004427 A1 | 1/2005 | Cervigni |
| 2005/0043580 A1 | 2/2005 | Watschke et al. |
| 2005/0143618 A1 | 6/2005 | Anderson et al. |
| 2005/0245787 A1 | 11/2005 | Cox et al. |
| 2005/0250977 A1 | 11/2005 | Montpetit et al. |
| 2005/0283189 A1* | 12/2005 | Rosenblatt ......... A61B 17/0401 606/216 |
| 2006/0016866 A1 | 1/2006 | Oakes et al. |
| 2006/0089525 A1* | 4/2006 | Mamo ................ A61B 17/0401 600/37 |
| 2006/0195011 A1 | 8/2006 | Amal et al. |
| 2006/0224038 A1 | 10/2006 | Rao |
| 2006/0260618 A1 | 11/2006 | Hodroff et al. |
| 2007/0062541 A1 | 3/2007 | Zhou et al. |
| 2007/0149555 A1 | 6/2007 | Kase et al. |
| 2007/0299299 A1* | 12/2007 | Rosenblatt ....... A61B 17/06166 600/30 |
| 2008/0021265 A1 | 1/2008 | Garbin et al. |
| 2008/0027271 A1 | 1/2008 | Maccarone |
| 2008/0045782 A1 | 2/2008 | Jimenez |
| 2010/0105979 A1 | 4/2010 | Hamel et al. |
| 2010/0261952 A1 | 10/2010 | Montpetit et al. |

FOREIGN PATENT DOCUMENTS

| | | |
|---|---|---|
| EP | 2649961 A1 | 10/2013 |
| EP | 2170217 B1 | 2/2017 |
| WO | 2003/077772 A1 | 9/2003 |
| WO | 2003096929 A1 | 11/2003 |
| WO | 2004/045457 A1 | 6/2004 |
| WO | 2005/110274 A2 | 11/2005 |
| WO | 2005/122954 A1 | 12/2005 |
| WO | 2006/069078 A2 | 6/2006 |
| WO | 2007016083 A1 | 2/2007 |
| WO | 2007/059368 A1 | 5/2007 |
| WO | 2007/081955 A1 | 7/2007 |
| WO | 2007097994 A2 | 8/2007 |
| WO | 2007/146784 A2 | 12/2007 |
| WO | 2007/149348 A2 | 12/2007 |
| WO | 2007149555 A2 | 12/2007 |
| WO | 2008/013867 A1 | 1/2008 |
| WO | 2008/015722 A1 | 2/2008 |
| WO | 2008/042438 A2 | 4/2008 |
| WO | 2008/057269 A1 | 5/2008 |
| WO | 2008/083394 A2 | 7/2008 |
| WO | 2008/124056 A1 | 10/2008 |
| WO | 2009/005714 A2 | 1/2009 |
| WO | 2009/011852 A1 | 1/2009 |
| WO | 2009/038781 A1 | 3/2009 |
| WO | 2009/075800 A1 | 6/2009 |
| WO | 2009/145911 A1 | 12/2009 |
| WO | 2010/129331 A2 | 11/2010 |

\* cited by examiner

SURGICAL ARTICLES AND METHODS FOR TREATING PELVIC CONDITIONS

CROSS-REFERENCE TO RELATED APPLICATIONS

This application is a Continuation of, and claims priority to, U.S. patent application Ser. No. 12/666,953, filed on Oct. 1, 2010, entitled "SURGICAL ARTICLES AND METHODS FOR TREATING PELVIC CONDITIONS", which claims the benefit from International Patent Application No. PCT/US2008/008006, which was filed on 27 Jun. 2008, which in turn claims priority to U.S. Provisional Patent Application No. 60/947,044, filed Jun. 29, 2007, entitled "PELVIC FLOOR TREATMENTS AND ASSOCIATED IMPLANTS," the disclosures of which are incorporated by reference herein in their entireties.

FIELD OF THE INVENTION

The invention relates to apparatus and methods for treating pelvic conditions by use of a pelvic implant to support pelvic tissue. The pelvic conditions include conditions of the female or male anatomy such as treatments that involve supporting levator muscle to treat female or male fecal incontinence, among other conditions

BACKGROUND

Pelvic health for men and women is a medical area of increasing importance, at least in part due to an aging population. Examples of common pelvic ailments include incontinence (fecal and urinary), and pelvic tissue prolapse (e.g., female rectal and vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse as well as perineal descent. A cystocele is a hernia of the bladder, usually into the vagina and introitus. Pelvic disorders such as these can result from weakness or damage to normal pelvic support systems.

Pelvic implants, sometimes referred to as slings, hammocks, have been introduced for implantation in the body to treat pelvic conditions such as prolapse and incontinence conditions. See, for example, commonly assigned U.S. Pat. Nos. 6,382,214, 6,641,524, 6,652,450, and 6,911,003, and publications and patents cited therein. The implantation of these implants involves the use of implantation tools that create transvaginal, transobturator, suprapubic, transperineal, transrectal, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the BioArc™ SP and SPARC™ single use sling implantation tools sold in a kit with an elongated urethral sling by American Medical Systems, Inc. One specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. In addition, damage or weakness in ligament structures such as the transverse perineal ligaments, anococcygeous ligament, arcus tendineous, sacrospinous, cardinal, and sacrotuberal ligaments may also alter their supportive nature and alter anatomy and cause pelvic floor symptoms. For various reasons, the levator and ligaments may suffer weakness or injury that result in various symptoms such as prolapse, incontinence, and other conditions of the pelvis.

SUMMARY

The invention relates to methods of treating pelvic conditions, including those referenced above, such as urinary and fecal incontinence, conditions of the pelvic floor, and combinations of these.

Embodiments of the inventive methods relate to treating levator defects. Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence. Perineal descent of the levator hiatus is also believed to play a significant role in the progression of prolapse. Embodiments of methods of the invention can address any of the conditions, as well as related conditions and symptoms.

The present patent application describes pelvic implants and methods for treating pelvic conditions. Examples of methods treat defects of the pelvic floor (coccygeus or levator), such as weakness or injury, by supporting levator muscle. Useful methods can involve methods and implants that can restore natural pelvic floor anatomy using an implant (e.g., graft) in the form of a hammock, sling, and the like, to augment injured, weakened, or attenuated levator musculature. The levator musculature or "levator ani" can include the puborectalis, pubococcygeus, iliococcygeus.

Embodiments of implants useful according to the invention can be of a size and shape to address a desired pelvic floor condition such as urinary incontinence, fecal incontinence, or conditions of the pelvic floor. Exemplary implants may include a frame, as described herein, or a bearing for engaging a spreader during implantation.

Exemplary implants can be of a size and shape to conform to pelvic tissue, such as levator tissue, optionally to contact or support other tissue of the pelvic region such as the anal sphincter, rectum, perineal body, etc. The implant can be of a single or multiple pieces that is or are shaped to match a portion of the levator, e.g., that is circular, oblong trapezoidal, rectangular, that contains a combination of straight, angled, and arcuate edges, etc. The implant may include attached or separate segments that fit together to extend beside or around pelvic features such as the rectum, anus, vagina, and pelvic floor ligaments, and the like, optionally to attach to the feature.

An implant for use in treating a condition of the pelvic floor (e.g., fecal sling) can be a continuous or a non-continuous sling, and can include one or multiple pieces or segments, e.g., an integral continuous implant or an assembly of segments. A continuous implant may be substantially continuous between edges, to be placed over a substantially continuous or level surface area of levator tissue. A non-continuous implant may include breaks or cuts that allow much of the implant to be placed on a level or continuous surface of levator tissue, with portions being formed to extend around tissue structure extending from or to the levator tissue, such as the anus, rectum, etc. The implant can include a tissue support portion, which at least in part contacts levator tissue. Optionally, the implant can additionally include one or more extension portion that extends beyond the tissue support portion and to be secured to tissue of the pelvic region to support the tissue support portion.

Optionally, extension portions can include features such as a tissue fastener (e.g., self-fixating tip, soft tissue anchor, bone anchor, etc.), a sheath, a tensioning mechanism such as a suture, an adjustment or locking mechanism such as a plastic (e.g., polypropylene) locking eyelet or grommet used in combination with a mesh arm, etc.

An implant, including a tissue support portion and optionally an extension portion, tissue fastener, etc., may optionally be coated with antimicrobial coatings to prevent infection or coatings to encourage ingrowth or inhibit rejection. For tissue support portions and extension portions, biocompatible materials are contemplated such as porcine dermis or meshes with growth factors.

Methods described herein may improve or treat a condition of the pelvic region. Examples of methods involve the use of an implant that includes a frame, which is a discrete element of an implant that improves the ability of an implant to become spread open when the implant is being installed within a pelvic region of a patient. In addition, a frame, upon being installed, can provide additional support to tissue being supported, such as to a pelvic floor, vaginal tissue, urethral tissue, etc. Other examples of methods involve the use of a spreader tool to place the implant within a pelvic region of a patient, the spreader tool being useful to spread the implant within the patient; the spreader tool may cooperate with an optional bearing located on an implant to facilitate engagement of the spreader tool with the implant. A frame, a spreader, or both, can be useful to place an implant in a spread (i.e., flat, unfolded, unrolled, un-bunched) configuration. Among other advantages, a spreader, frame, or a combination of these, can allow implant material (especially a mesh) to be installed to lay flat with no bunching, folding, or rolling, any of which may prevent effective tissue integration. Also, the use of a spreading tool, frame, or placed on a level or continuous surface of levator tissue, with portions being formed to extend around tissue structure extending from or to the levator tissue, such as the anus, rectum, etc. The implant can include a tissue support portion, which at least in part contacts levator tissue. Optionally, the implant can additionally include one or more extension portion that extends beyond the tissue support portion and to be secured to tissue of the pelvic region to support the tissue support portion. Optionally, extension portions can include features such as a tissue fastener (e.g., self-fixating tip, soft tissue anchor, bone anchor, etc.), a sheath, a tensioning mechanism such as a suture, an adjustment or locking mechanism such as a plastic (e.g., polypropylene) locking eyelet or grommet used in combination with a mesh arm, etc.

An implant, including a tissue support portion and optionally an extension portion, tissue fastener, etc., may optionally be coated with antimicrobial coatings to prevent infection or coatings to encourage ingrowth or inhibit rejection. For tissue support portions and extension portions, biocompatible materials are contemplated such as porcine dermis or meshes with growth factors.

Methods described herein may improve or treat a condition of the pelvic region. Examples of methods involve the use of an implant that includes a frame, which is a discrete element of an implant that improves the ability of an implant to become spread open when the implant is being installed within a pelvic region of a patient. In addition, a frame, upon being installed, can provide additional support to tissue being supported, such as to a pelvic floor, vaginal tissue, urethral tissue, etc. Other examples of methods involve the use of a spreader tool to place the implant within a pelvic region of a patient, the spreader tool being useful to spread the implant within the patient; the spreader tool may cooperate with an optional bearing located on an implant to facilitate engagement of the spreader tool with the implant. A frame, a spreader, or both, can be useful to place an implant in a spread (i.e., flat, unfolded, unrolled, un-bunched) configuration. Among other advantages, a spreader, frame, or a combination of these, can allow implant material (especially a mesh) to be installed to lay flat with no bunching, folding, or rolling, any of which may prevent effective tissue integration. Also, the use of a spreading tool, frame, or and attached at the arcus tendineus; obturator internus muscle. Alternately, an extension portion of an implant can be extended through a tissue path that leads to an external incision such as: by passing through tissue of the obturator foramen to pass through an external incision at the inner thigh; passing above the pubic bone to exit at a suprapubic incision; passing in a posterior direction to an external perirectal or perianal incision, e.g., past the coccyx bone. As another alternative, an implant or extension portion of an implant can be attached to bone or fascia thereof, such as the sacrum or pubic bone, or fascia thereof.

According to exemplary methods, an implant can be introduced through an incision that allows access to pelvic tissue, optionally with some amount of dissection. The incision can be any of a variety of incisions that provides such access, such as a small external perirectal incision that can allow a tissue path to extend from the external perirectal incision to levator tissue; an external suprapubic incision; an external incision at an inner that can be used to pass a portion of an implant through an obturator foramen, a Kraske incision under the rectum; an incision at the perineum; an incision at the inner groin or thigh adjacent to an obturator foramen; and a vaginal incision. An implant or a portion of the implant can be accessed or placed into position using the incision and optional dissection, to support tissue of the pelvic region. For placing an implant to contact tissue of the pelvic floor, the implant can preferably be placed by dissecting a plane or region of dissection that includes the ischorectal fossa. Anatomical landmarks included with this region of dissection can include the ischial spine, the obturator internus, the arcus tendineus.

One embodiment of implant can be a synthetic or biologic implant having a tissue support portion. The tissue support portion can be sized and shaped to support desired tissue of the pelvic region, such as vaginal tissue, urethral tissue, tissue of the bladder, tissue of the rectum or anus, levator tissue, etc. The precise form can depend on the type of condition being treated. Certain embodiments of a tissue support portion may optionally include a segment or support for addressing levator hiatus opening, perineal descent, rectal prolapse, fecal incontinence, etc. An implant for use in contacting any of these tissues can optionally include a bearing or a frame as described herein.

An implant may optionally but not necessarily include extension portions that extend to other tissue, e.g., in the pelvic region, sometimes referred to as "supportive tissue," to which the extension portion may be secured in a manner to allow the extension portion to support the tissue support portion. Also optionally, ends of extension portions can include a tissue fastening mechanism such as a self-fixating tip that can be secured to internal tissue of the pelvic region such as described elsewhere herein, including but not limited to tissue of: sacrotuberous ligament, sacrospinous ligament, periostium of the pubic bone (e.g., in a region of the ischial tuberosity), a region of the ischial spine, ischial tuberosity, pubourethral ligament, anococcygeal body ligament, and arcus tendineus; or through a tissue path between levator ani muscle and obturator internus muscle and attaching the extension portion at the arcus tendineus or obturator tissue (e.g., obturator internus), or passing through tissue of the obturator foramen. The extension portion of the implant can optionally include a bearing or a frame as described herein.

Certain embodiments of the invention contemplate methods of supporting levator tissue. Exemplary such methods include steps that involve creating a single medial incision (a transvaginal incision or a perineal incision) or an incision near the rectum, anus, or perineum; and dissecting within a plane or region of dissection including the ischorectal fossa. An implant can be inserted to contact tissue of the levator, over a desired area. Optionally, the implant can be a single piece or multiple pieces or portions, and may include one or more tissue fasteners that can be secured to tissue in the pelvic region. An implant may include materials or components such as those used in the SPARC and Monarc systems (from American Medical Systems), include connectors for engagement between a needle of an insertion tool and an distal end of an extension portion, as well as helical, straight, and curved needles.

The invention furthermore contemplates embodiments of methods and apparatus for treating pelvic conditions that involve a single incision whereby the implant does not exit through another skin incision such as an abdominal or leg incision, for treating any pelvic condition.

In one aspect, the invention relates to a method of supporting tissue of the pelvic region. The method includes: creating an incision that allows access to the pelvic region, providing a pelvic implant comprising a tissue support portion and an extension portion extending from the tissue support portion, providing a spreader tool comprising a handle, an elongate shaft having a distal end, and a spreader at the distal end of the shaft, passing the implant through the incision and placing the tissue support portion at the region of pelvic tissue, positioning the tissue support portion at the region of the pelvic floor tissue in a manner to cause the tissue support portion to support tissue of the pelvic floor, inserting the spreader through the incision to locate the spreader at a location of the implant, and using the spreader to spread material of the implant.

In another aspect the invention relates to a method of supporting tissue of the pelvic region, the method comprising creating an incision that allows a pelvic region, providing a pelvic implant comprising a tissue support portion, an extension portion extending from the tissue support portion, and an elongate frame; passing the implant through the incision and placing the tissue support portion at the pelvic region, positioning the tissue support portion to cause the tissue support portion to support pelvic tissue.

In another aspect, the invention relates to a pelvic implant that includes a tissue support portion, an extension portion, and an elongate frame.

In another aspect, the invention relates to a kit that includes an implant and a spreader tool. The spreader tool includes a handle, an elongate shaft having a distal end, and a spreader at the distal end of the shaft. The implant includes a tissue support portion and an extension portion.

BRIEF DESCRIPTION OF DRAWINGS

Other features and advantages of the present invention will be seen as the following description of particular embodiments progresses in conjunction with the drawings. Drawings are schematic and not to scale.

DETAILED DESCRIPTION

Figure 1:
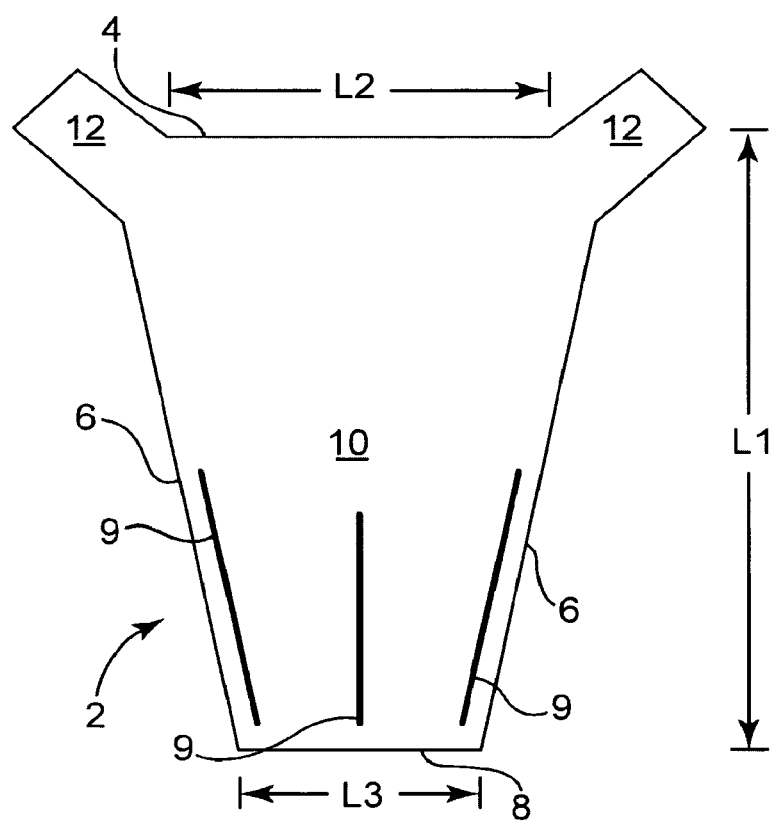
FIG. 1 illustrates an embodiment of an implant as described.

The following description is meant to be illustrative only and not limiting. Other embodiments of this invention will be apparent to those of ordinary skill in the art in view of this description.

The invention relates to surgical instruments, assemblies, and implantable articles for treating conditions of the pelvic region, e.g., urinary incontinence, prolapse such as various types of vaginal prolapse (enterocele, rectocele, cystocele), as well as other types of pelvic conditions including pelvic floor disorders including fecal incontinence, conditions of the perineal body, conditions of levator muscle (such as a component of levator muscle), conditions of the levator hiatus, and combinations of two or more of these.

According to certain embodiments, a surgical implant can be used to treat urinary incontinence in male and female patients, e.g., by placing an implant to support tissue of the urethra or bladder neck. In other embodiments an implant can be used to treat vaginal prolapse such as enterocele, cystocele, rectocele, vaginal vault prolapse, etc., by placing an implant to support vaginal tissue. Methods that may be useful for placing these types of implants can involve trans-abdominal, transvaginal, perineal, and trans-obturator tissue paths.

According to other embodiments, a surgical implant can be used to treat a pelvic condition, wherein the method includes placing an implant in a manner that support tissue of the pelvic floor, including one or more of levator muscle and coccygeus muscle, in males or females. Various aspects of the invention are described as embodied by features of surgical implants, surgical tools, surgical systems, surgical kits, and surgical methods, useful for implants and for installing implants.

Regarding methods of treating a condition of the pelvic floor, defects of the pelvic floor such as levator muscle distension or ballooning may have a significant effect on perineal body descent and acute, potential, impending, or future pelvic prolapse, as well as prolapse recurrence. One embodiment of the invention involves methods by which tissue of the pelvic floor (e.g., levator muscle, coccygeus muscle) can be supported to reduce this distension. This embodiment involves placing various materials subcutaneously against levator or coccygeus muscle; the placement can be made by any incision and dissection route, but particular methods involve incisions in the perirectal, perianal, and perineal regions and not necessarily by use of a transvaginal incision. (According to other embodiments, an implant can be placed tranvaginally.)

According to certain embodiments of the invention, tissue of the pelvic floor can be supported by an implant in the form of a mesh or biologic sling, hammock, or the like, similar to some of those that have been previously used to treat pelvic conditions such as forms of urinary incontinence, prolapse, fecal incontinence, etc., in men and women, optionally modified as described herein to incorporate a frame, one or more bearing as described for use in combination with a spreader, or both a frame and one or more bearing.

Other possible support mechanisms can be useful as well, other than those similar to such conventional pelvic implants, which may be considered "static." Examples of other support structures (i.e., "implants") include structures that are dynamic and not static. A dynamic implant can exhibit the ability to change after being implanted in a manner that can allow a dynamic function, such as dynamic support. The degree of support may be changed or adjusted at different stages of a disease or condition.

Examples of alternate support mechanisms (static or non-static) include but are not limited to: bulking agents (collagen, saline, silicone, etc.), expandable foam/insulation to fill volume, pillows filled with saline, silicone, or the like, that could be deflated and inflated to aid in defecation, sponges that could be combined with growth factors to facilitate ingrowth or used along to fill space.

Embodiments of methods that do not include vaginal dissection may be easier to perform and reduce risk and tissue trauma to the patient. This repair may be done during or after performing other treatments of the pelvic floor, such as to treat vaginal prolapse (e.g., vault prolapse, enterocele, rectocele, cystocele, etc.), may reduce the recurrence rate of vaginal prolapse (e.g., as addressed by products such as the Apogee™ and Perigee™ prolapse products from American Medical Systems, and similar products), and may provide an overall improvement when used in combination with or after other prolapse repair procedures. Alternately, certain procedures described herein may be used prophylactically to prevent future prolapse. The procedures may be performed before, after, or concurrently. with a hysterectomy, to potentially prevent or reduce the possibility or severity of subsequent prolapse. In other embodiments, a method as described may be useful following a prostatectomy or bladder removal (due to cancer), again to potentially prevent or reduce the possibility or severity of subsequent pelvic conditions.

Aspects of the invention relate to the use of an implant (e.g., polypropylene mesh), surgically implanted to support the levator muscles to reduce levator muscle distension, or to otherwise repair levator tissue. Techniques can involve delivering an implant (e.g., a mesh) to tissue of the levator and securing it into place to support the levator tissue. These procedures and devices involve placing an implant subcutaneously against the levator muscle (i.e., below or inferior to the levator muscle). This can be done transvaginally, but also can be done with an external incision in the perineal area (of the male or female anatomy), perirecta] area, or with other incision locations. In certain embodiments, the implant (either the tissue support portion or an extension portion) can also be secured to other tissue, i.e., "supportive tissue," of the pelvic region, to support the tissue support portion. Exemplary supportive tissue is described herein, for example at FIG. 6 and related text, and is described at other portions of the present description. Supportive tissue includes, tissue at an anterior location such as at the obturator foramen or arcus tendineus, or at a posterior location such as a region of the ischial spine or at a sacrospinous ligament.

The implant can be attached to supportive tissue in the pelvic region directly or by use of a tissue fasteners (e.g., anchors such as bone anchors, soft tissue anchors, self-fixating tips, tissue clamps, etc.). A tissue fastener may be attached to a tissue support portion or to an extension portion of an implant, and may be attached to either of these directly or by a connective suture. According to the latter, a tissue fastener can be placed and then material of the implant (e.g., mesh) may be guided along the suture lines as a track or guide to be tacked into place.

In alternate embodiments, an implant can be inserted through an external incision and attached as desired, e.g., near the external incision, such as an external incision in a perirectal region (e.g., for an implant used for treating posterior vaginal prolapse or conditions of the rectum), or an external incision in a region of the groin or inner thigh for a method that involves a transobturator tissue path.

Embodiments of certain implants can be of materials and designs that will be the same as or similar to implants conventionally useful for treatments of conditions of the pelvic region. An implant can include a tissue support portion (or "support portion") that can be used to support pelvic tissue, e.g., tissue of levator muscle, vagina, rectum, bladder, or urethra, etc. During use, the tissue support portion is typically placed in contact with tissue to be supported (e.g., levator tissue) and optionally in addition, to surrounding tissue such as tissue of the rectum, tissue of a perineal body, tissue of the external anal sphincter, to support one or more of these. Also optionally the tissue support portion can be attached to such tissue, for example as with a suture, biological adhesive, etc.

Embodiments of implants can optionally include one or more extension portions (also sometimes referred to as "end portions" or "arms") attached to the tissue support portion. Extension portions are pieces of material, for example elongate pieces of material, that extend from the tissue support portion and either are or can be connected to the tissue support portion, and are useful to attach to or pass through anatomical features in the pelvic region to provide support for the tissue support portion and the supported tissue. One or multiple (e.g., one, two, or four) extension portions can extend from the tissue support portion as elongate "ends," "arms," or "extensions," useful to attach to tissue in the pelvic region, such as by extending through a tissue path to an internal anchoring point as described herein. Optionally, according to alternate embodiments of the invention, the extension portion may pass through tissue of the pelvic region and to an external incision.

Embodiments of exemplary implants that may be useful as discussed herein can include a tissue support portion and no extension portions. Other embodiments can include one, two, three, or more extension portions attached to a tissue support portion. An exemplary urethral sling can be an integral mesh strip or hammock with supportive portions consisting of or consisting essentially of a central support portion and zero, one, or two extension portions.

An implant may include portions or sections that are synthetic or of biological material (e.g., porcine, cadaveric, etc.), and that may be resorbable or non-resorbable. Extension portions may be, e.g., a synthetic mesh such as a polypropylene mesh. The tissue support portion may be synthetic (e.g., a polypropylene mesh) or biologic.

The implant, either or both of the tissue support portion or an extension portion, may comprise variable weave meshes with varying elasticities such as a mesh that is highly elastic around the anus to allow stool to pass.

Some example of commercially available materials may include MarleX™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W. L. Gore and associates, Phoenix, Ariz., and the polypropylene sling material available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

Dimensions of an implant can be as desired and useful for any particular installation procedure, treatment, patient anatomy, to support a specific tissue or type of tissue, and to extend to a desired location of internal supportive tissue or an external incision.

Exemplary dimensions for implants used to support tissue of a pelvic floor can be sufficient to allow the tissue support portion to contact tissue of the levator, coccygeus, rectum, external anal sphincter, etc.; or any desired portion of one or more of these. Optionally, one or more extension portion can extend from the tissue support portion to a desired internal or external anatomical location to allow the extension portion to be secured to anatomy of the pelvic region, to support the tissue support portion.

Dimensions of extension portions can allow the extension portion to reach between a tissue support portion placed to support tissue of the pelvic region (at an end of the extension portion connected to the tissue support portion) and a location at which the distal end of the extension portion attaches to pelvic tissue, or may optionally pass through an external incision.

An implant can be of a single or multiple pieces that is or are shaped overall to match a portion of the levator, e.g., that is completely or partially circular, trapezoidal (non-symmetric or symmetric), rectangular, rhomboidal, etc. The implant may be multiple pieces to fit beside or around pelvic features such as the rectum or anus. Alternately, the implant may be irregular (while optionally symmetrical) to reach different areas of the levator.

An implant can be a continuous or a non-continuous sling, and of one or multiple pieces or segments. A continuous implant may be substantially continuous between edges, to be placed over a level surface area of pelvic (e.g., levator) tissue. A non-continuous implant may include breaks or cuts that allow much of the implant to be placed on a level surface of pelvic (e.g., levator) tissue, with portions being formed to extend around tissue structure extending from or to the pelvic tissue, such as the anus, rectum, etc.

An embodiment of a non-continuous sling may be designed to cover or contact area of the levator, coccygeus, or both, and also reach around to contact a posterior side of the rectum or external anal sphincter. For example, a portion of an implant could attach to the lateral sides of the external anal sphincter and extend toward or in the direction of the obturator foramen, or any other suspensory structure (e.g., supportive tissue), but need not engage tissue of the obturator foramen directly. In this embodiment, the tissue support portion of the implant need not necessarily be directly under the anus to provide the corrective action for fecal incontinence. An advantage to of this approach is to allow the anus to expand unrestricted to facilitate normal rectal function and may give the levator plate (or plates) the support necessary to be leveraged.

Embodiments of implants can include a segment that is located anterior to the anus, such as in contact with levator tissue or tissue of the perineal body, anterior to the anus. Alternate implants may be designed to replace the perineal muscle or attach to the superior portion of the external sphincter. The various embodiments disclosed herein are also applicable to men and can be implanted via an incision in the peririeal floor (see attached figures).

An implant can also include a frame to give_shape or support to an implant (i.e., a "stiffener," "strut," or "support," etc.). A frame can be located at a surface or edge of an implant to cause the implant to spread out to a desired shape upon placement within a patient. As used herein, the term "spread" refers to an implant or a spreader that is in an open, e.g., unfolded, configuration; likewise, the term "unspread" refers to an implant or a spreader that is either to some degree folded or rolled onto itself.

A frame provides added shape-retention to facilitate placement of an implant at a desired position within a patient, so the implant can take on a spread configuration to achieve full size and to cover a fully-expanded area without unwanted folding. According to specific embodiments, a frame can be placed in alignment with or parallel to, and near, an edge of an implant (e.g., within 0.5 centimeter, or within 0.3 centimeters, and extending along a continuous edge).

A frame may be a discrete element of an implant that is more rigid than the implant material (mesh or biologic material), and may be shaped and incorporated into the structure of the implant to improve the ability of the implant to take on and maintain a spread configuration upon being placed within a pelvic region of a patient. A frame may be a plastic material such as a plastic strip that is attached to an implant along an edge or along a length of a surface of an implant. The frame can optionally be flexible to some degree, yet still provide a degree of rigidity that prevents the implant from becoming folded or maintaining a folded position in a direction that would fold or bend the frame. The frame can be straight, curved, or cornered, and optionally biased, e.g., in a spring-like fashion. The frame can be placed along a single edge of an implant, along opposing edges, or one or more frame can be placed along multiple edges of an implant or a portion of an implant, extending around a perimeter or a portion of a perimeter of an implant or a portion of an implant. As yet another alternative, one or more frames can be used to shape and support (e.g., stiffen) a surface area of an implant or a portion of an implant by being placed at a surface of the implant away from edges.

Certain previous types of reinforcements or tensioning members have been used with pelvic implants to add tensile strength, such as a suture or plastic sheath (or sleeve) extending along a length of an extension portion of an implant to provide tensile strength in a length-wise direction. Such reinforcement or tensioning member generally functions to allow the implant to be pulled through a tissue path without stretching the implant material. A frame as described herein can provide more than merely this type of increased tensile strength, and in fact does not necessarily provide this type of increased tensile strength. Functionally, embodiments of frames can be sufficiently rigid to maintain the shape of an implant and to allow the implant to return substantially to an original shape after bending in a direction that flexes the frame. For example, embodiments of frames may prevent an implant from maintaining a fold in a direction that flexes the frame (without causing permanent deformation of the frame). In an alternate functional sense, a frame can allow an implant to fold in a direction that bends the frame (without permanently deforming the frame), and when released from the bent condition the frame will cause the implant to return at least to a major degree to the un-flexed state. Preferably the frame substantially returns to the original shape of the frame.

A frame can be made of any useful material that is more rigid than an implant material, preferably that is sufficiently rigid to prevent folding along an edge or surface of an implant. Exemplary materials include polymeric or non-polymeric materials that can be molded or formed to a desired shape and attached to an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

The shape of the frame can be any shape that can be placed at an edge or a surface of an implant to cause the implant to maintain a desired open form. A frame is elongate so the frame causes the implant to spread over a length of the frame. A frame may be in the form of a straight or curved slat, rod, bar, brace, girder, strut, or the like, that exhibits rigidity with optional flexibility in three dimensions. The frame can preferably allows some degree of bending but still be sufficiently rigid to maintain an implant in a straight or slightly curved configuration. The frame may have a round or cornered cross section. A frame may be capable of being substantially bent or coiled, then opened. For example a metal or plastic material may be sufficiently flexible to be rolled (e.g., coiled) or folded up within a rolled or folded implant, without permanent deformation. The implant can be un-folded or un-rolled, and the unfolded or unwound frame will maintain the open shape of the implant.

The frame can be attached to implant material by any desired method, such as by mechanical securement (e.g., sutures, staples), adhesive, thermobonding, by weaving the frame into the mesh, or by creating a fold, loop, or pocket that is sized to fit the frame.

Optionally or preferably, one or more frames can be sized, shaped, and placed on an implant, in an arrangement to allow the implant can be folded (without permanently deforming a frame) to a size that will fit through a small skin or vaginal incision, such as a vaginal or skin incision that is no more than 3 centimeters in length (e.g., a Krasky incision, or other skin incision described herein). For example, frames may be aligned or parallel, optionally of similar shape (e.g., identically curved or straight), optionally but not necessarily of equal lengths. The frames maybe spaced apart from each other when the implant is unfolded, but the implant may be folded so the frames take up only a small amount of cross-sectional space, and can be fit length-wise through a small aperture such as an external skin incision. Examples of frames used to support a shape of an implant are shown at the figures.

Figure 9A:
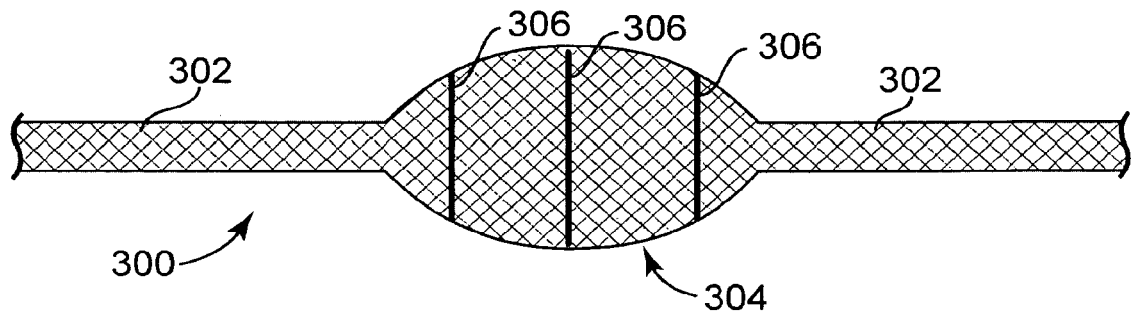
FIGS. 9A and 9B illustrate embodiments of implants that include frames.
Figure 9B:
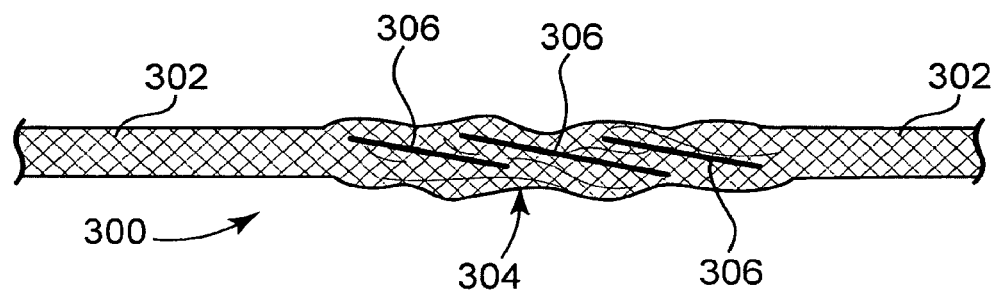

Referring to FIG. 9A, implant 300 includes tissue support portion 304 (illustrated as an oval or oblong shape) and two extension portions 302 extending in opposite directions away from tissue support portion 304. (Each extension portion may or may not include a self-fixating tip, which is not illustrated, as described elsewhere herein.) Frames 306, three of these, are placed at tissue support portion 304 to maintain a spread-out surface area of portion 304. In this embodiment, three frames are located in parallel to each other, and when unfolded, maintain tissue support portion 304 in an open position. FIG. 9B shows implant 300 in a folded state in which frames 306 are folded against each other to reduce the cross-sectional profile of the implant and allow the implant to be inserted through a small incision (e.g., a vaginal incision or an external skin incision). Once the folded implant is passed through an incision and located at a desired position in the pelvic region, the tissue support portion can be unfolded by any desired method and the frames will assist in maintaining the open state of the tissue support portion, preventing the tissue support portion from becoming re-folded.

Figure 10A:
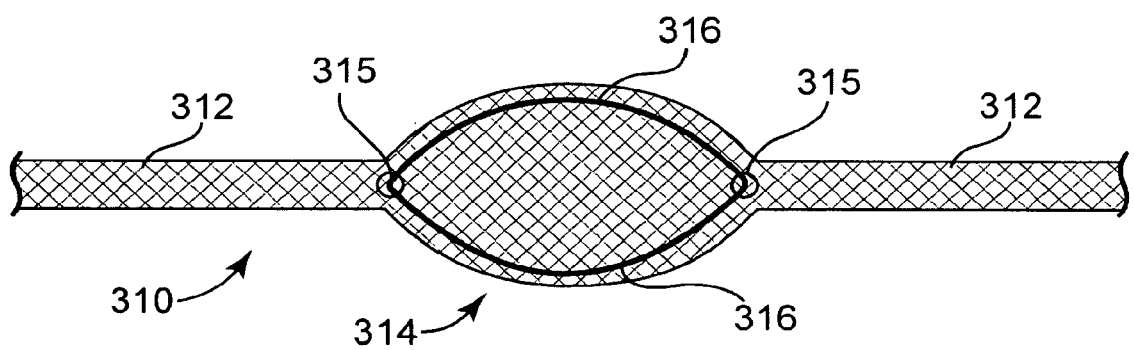
FIGS. 10A and 10B illustrate embodiments of implants that include frames.
Figure 10B:
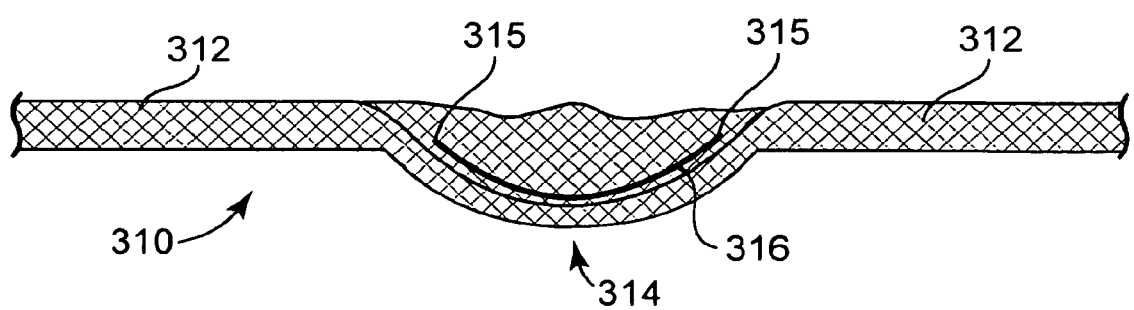

Another embodiment of an implant that includes frames is at FIGS. 10A and 10B. Implant 310 includes tissue support portion 314 (illustrated as an oval or oblong shape) and two extension portions 312 extending in opposite directions away from tissue support portion 314. (Each extension portion may or may not include a self-fixating tip, which is not illustrated, as described elsewhere herein.) Frames 316, two of these, are placed at tissue support portion 314 to maintain a spread-out surface area of portion 304. The two opposing frames may be connected or unconnected and are illustrated as being connected at connections 315 at each of the ends of frames 316. The connection may be hinged, or optionally may be biased or to cause the two opposing frames to maintain an opened configuration as illustrated at FIG. 10A.

FIG. 10B shows implant 310 in a folded state in which frames 316 are folded against each other to reduce the cross-sectional profile of the implant and allow the implant to be inserted through a small incision. Once the folded implant is passed through an incision and located at a desired position in the pelvic region, the tissue support portion can be unfolded by any desired method and frames 316 will assist in maintaining the open state of the tissue support portion, preventing tissue support portion 314 from becoming re-folded. In one specific embodiment, frames 316 may be biased to an open position (FIG. 10A) and held together in a closed position (FIG. 10B). FIG. 10B does not show a mechanism that holds frames 316 together, but any temporary mechanism could be used such as a suture or plastic or metal clip that could be removed upon placement of the implant. Preferably the suture or clip could be removed by the user by a mechanism that is external to the patient. For example a lead (e.g., a suture) could extend from frames 316 or a clip attached to frames 316, to an external location, and the lead could be pulled by a surgeon to release frames 316 to open from a closed to an opened configuration.

As another option that may be included separately or in combination with other features of an implant, an implant can also include a bearing, preferably two bearings. A bearing can be a surface that is capable of engaging a spreader to allow the spreader to apply pressure to the implant to spread (i.e., unfold) the implant, and to optionally unspread (fold) the implant. A bearing can be configured to correspond to and engage a portion of a spreader in a manner that is sufficiently secure to allow the spreader to spread the implant. Optionally and preferably an implant can include multiple bearings, such as two, that can each be engaged by a different portion of a spreader, so the spreader can spread the implant between the two bearings.

An exemplary bearing can allow for temporary engagement between an implant and a spreader in a manner that allows the spreader to either spread (unfold) or optionally unspread (fold) an implant. A specific example of an bearing is a hole in an implant that can engage a pin at a spreader of a tool. Additional examples include a fold, a seam, a sheath, a suture, a loop, and a pocket formed by a suture or a fold, any of which can be engaged by a surface of a spreader to allow the spreader to spread an implant when placing the implant at a location in the pelvic region.

Figure 16A:
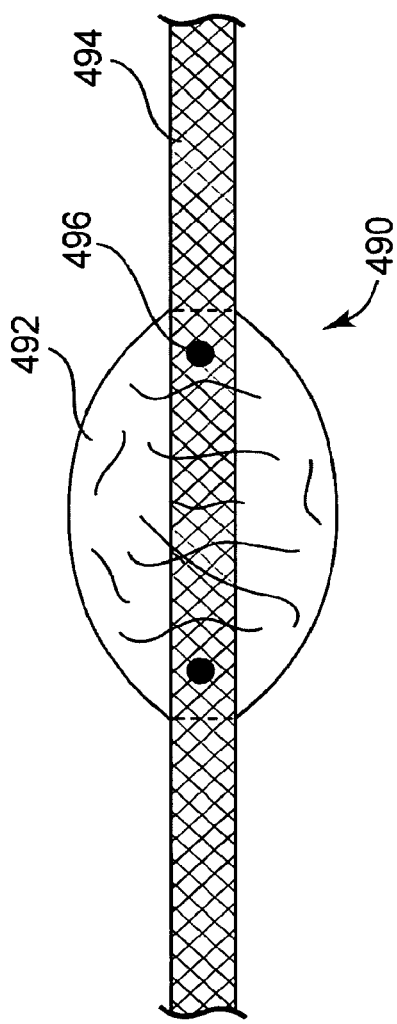
FIGS. 16A and 16B illustrate embodiments of implants.
Figure 16B:
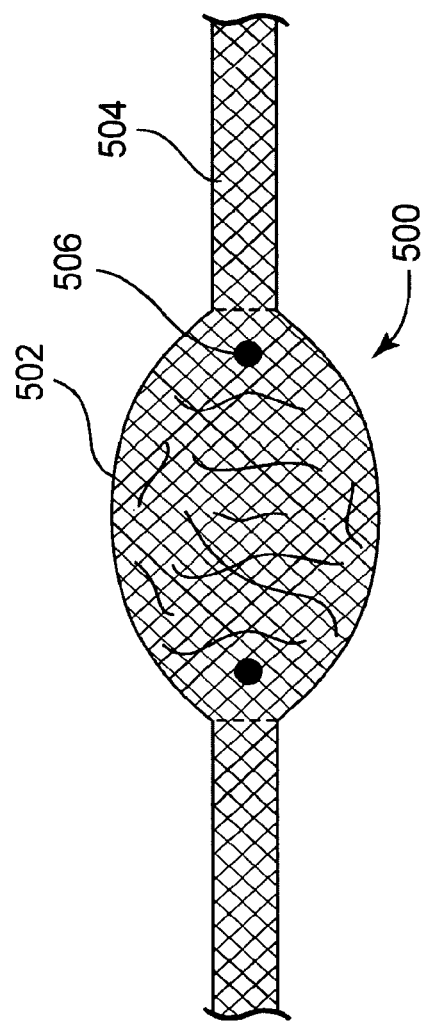

FIGS. 16A and 16B show additional examples of implants, these not showing frames, although a frame may optionally be included in either implant. Implant 490 of 16A includes tissue support portion 492, extension portions 494, and polymeric rivets 496 that secure the tissue support portion to the extension portions. Tissue support portion 492 is made of a biologic material and has a relatively oval shape for support of pelvic tissue. The biologic implant material can exhibit advantageous mechanical properties relative to a simple mesh, such as greater stiffness to facilitate a flat and unfolded orientation upon placement. A biologic material for a tissue support portion may also buffer against tissue erosion or extrusion.

Implant 500 of FIG. 16B includes tissue support portion 502, extension portions 504, and polymeric rivets 506 that secure the tissue support portion to the extension portions. Tissue support portion 502 is made of a biologic material and has a relatively oval shape for support of pelvic tissue. Tissue support portion 502 includes a mesh that matches the size and shape of the biologic material.

An implant, e.g., at a tissue support portion or at a distal end of an extension portion, can optionally include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. Exemplary tissue fasteners are discussed, e.g., in PCT/SU2007/014120 "Surgical Implants, Tools, and Methods for Treating Pelvic Conditions, filed Jun. 15, 2007; the entirety of which is incorporated herein by reference. The implant may also have extension portions that do not include a tissue fastener at a distal end thereof, for example if the distal end is designed to be secured to tissue by other methods (e.g., suturing), or is intended to pass through a tissue path ending in an external incision.

An extension portion can be attached to any desired tissue of the pelvic region, or passed through a desired tissue path to an external incision. To attach an extension portion to tissue, a tissue fastener can optionally be attached at the distal end of the extension portion. During installation of the implant, the tissue fastener can be attached to any desired tissue, e.g., supportive tissue, many examples of which are described herein. Supportive tissue can be fibrous tissue such as a muscle (e.g., obturator foramen, especially the obturator internus; obturator externus; ligament such as the sacrotuberous ligament, sacrospinous ligament, or surrounding tissue; a tendon such as the arcus tendineus or surrounding tissue; or tissue at or near the ischial spine (i.e., at a region of the ischial spine) such as the ischial tuberosity.

A length of an extension portion (extended through any tissue path) can optionally be fixed or adjustable, allowing a surgeon to alter the length of an extension portion before, during, or after implantation. On the other hand, adjustment and tensioning mechanisms can also be excluded from embodiments of implants or from particular extension portions, e.g., superior extension portions that will attach to an obturator foramen, or extension portions that will be placed at a tissue path extending to an external incision.

A length of an extension portion can be sufficient to allow the distal end to reach desired tissue within or external to the pelvic region, e.g., from about 1 centimeter (cm) to about 5 centimeters. A width of the extension portion can be as desired, such as within the range from about 1 to 1.5 centimeters.

A "self-fixating tip" in general can be a structure connected to a distal end of an extension portion that can be implanted into tissue in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through tissue for implantation. The self-fixating tip may engage the insertion tool at an internal channel of the self-fixating tip, at an external location such as at a cylindrical base, or at a lateral extension, as desired. Exemplary self-fixating tips are described, for example, in PCT/US2007/004015 "Surgical Articles and Methods for Treating Pelvic Conditions," filed Feb. 16, 2007, the entirety of which is incorporated herein by reference.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

A self-fixating tip may be of any form that can be inserted into tissue of a pelvic region, and that will thereafter be retained in the tissue. Exemplary self-fixating tips can include one or more lateral extensions that can increase the force required to remove the self-fixating tip from tissue after insertion into the tissue, i.e. the "pullout force." At the same time, the lateral extensions can be designed to exhibit a reduced or relatively low "insertion force," which is the amount of force used to insert the self-fixating tip into tissue. The self-fixating tip can be designed to be essentially permanently placed upon insertion into tissue, with the single exception that if absolutely necessary to provide desired placement of the self-fixating tip or an attached implant, the self-fixating tip may be removed by a surgeon during an implantation procedure. The self-fixating tip, and all components of the self-fixating tip, can be of combined form and dimensions to result in these functional features.

According to exemplary embodiments, a self-fixating tip can have structure that includes a base having a proximal base end and a distal base end. The proximal base end can be connected (directly or indirectly, such as by a connective suture) to a distal end of an extension portion, or directly to a tissue support portion of an implant. The base extends from a proximal base end to a distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as, for example, by use of an insertion tool that contacts the self-fixating tip at an external location such as by grasping the base (on a side or at the face of the proximal base end) or by contacting a lateral extension.

Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be connected to an implant, such as at an extension portion of an implant, or to a tissue support portion, in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006-0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

An example of an implant is shown at FIG. 1. Implant 2, including tissue support portion 10, is generally in the form of a symmetric apezoid (with added extension portions 12), but may alternately be a symmetric rectangle, a rhombus, a square, a non-symmetric trapezoid, an oblong rectangle, or the like. Two extension portions 12 are located at corners that connect wide end 4 to sides 6. Sides 6 extend and terminate at narrow end 8. Tissue fasteners (not shown) can be placed at extension portions 12. In use, an extension portion can be attached to tissue of the pelvic region; for example one of tissue extension portions 12 can be attached to tissue in a posterior location such as a region of the ischial spine, sacrospinous ligament, ischiorectal fossa, or iliococcygeous muscle; the other extension portion can be attached at an anterior location such as at tissue of the obturator foramen, e.g., the obturator internus muscle near the inferior pubic ramus, tissue of the arcus tendineus, etc. This places long end 4 at a lateral position. Tissue support portion 10 extends medially below levator tissue and short end 8 becomes located at a medial position. Short end 8 can be placed, for example, under the rectum. When so placed the implant extends from lateral positions between a region of the ischial spine or sacrospinous ligament, to a region of the obturator foramen or arcus tendineus, with tissue support portion 10 in contact with levator tissue, and with short end 8 at a medial position, e.g., near the rectum, optionally under the anococcygeal body ligament.

Implant 10 includes three (optional) frames, 9. As illustrated, these are located at the narrowed end of tissue support portion 10, with their length extending generally in the direction of sides 6. Frames 9 are generally straight and point in opposite directions at short end 8 and wide end 4. In the illustrated embodiment, frames 9 are placed at a location on the surface and edges of tissue support portion 10, that will be located near the rectum when implanted at a patient's pelvic region. FIG. 1 shows three frames, but more or fewer could be included. Also, FIG. 1 shows that frames extending in a length approximately parallel with sides 6, but the frames could be placed in any direction, such as parallel to end 4 or end 8.

Lengths of the ends and sides can be as desired to allow for this placement. For example, length L1 can be in the range from 6 to 12 centimeters, such as from 7 to 10 centimeters. Length L2 of wide end 4 (not including extension portions 12) can be, e.g., from 3 to 5 centimeters. Length L3 of narrow end 8 can be, e.g., from 2 to 3 centimeters.

According to methods of the invention, implant 2 can be inserted through a medial incision, such as at the perineum, and placed as described, below levator tissue. Implant 2 is placed on one side of the pelvic floor to support substantially one side or half of levator muscle. A second implant of the same design can be placed to support the contralateral side, according to the same method. In this embodiment of implant and method, two separate implants are used, one below each side of the levator muscle, with short ends extending to a medial location. Preferably, the implants are also located below the superficial transverse perineal muscle. The short ends may overlap or be secured to each other or to tissue of the pelvic region, e.g., by a suture or other securing means such as adhesive, staples, etc.

Figure 2:
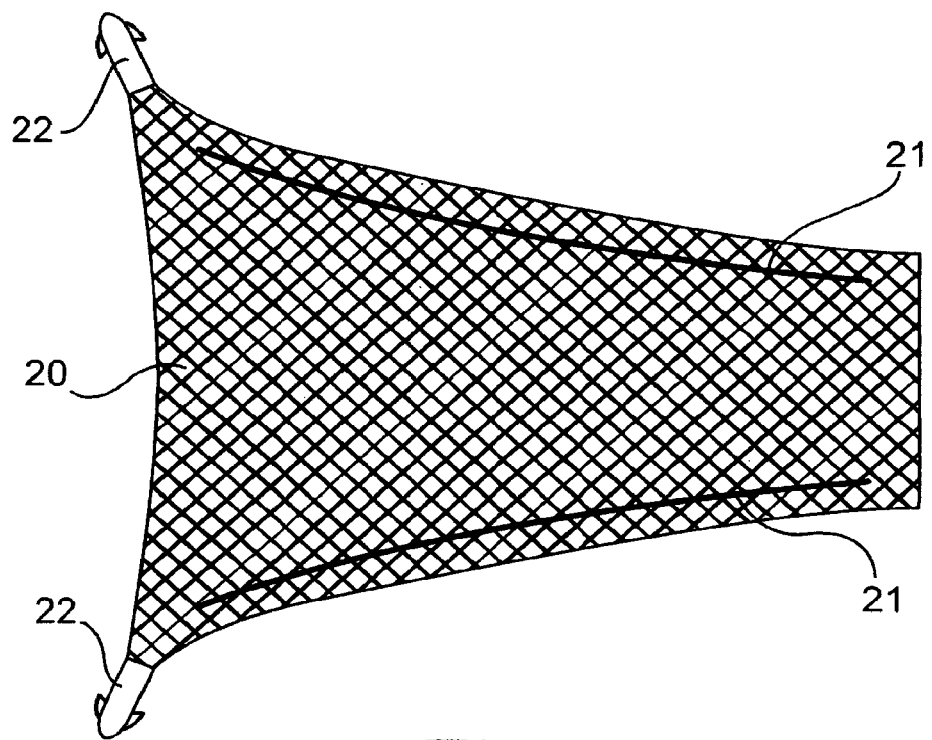
FIG. 2 illustrates an embodiment of an implant as described.

In FIG. 1, implant 12 can be a synthetic or a biologic material. FIG. 2 shows an example of an implant, 20, of synthetic mesh. Self-fixating tips 22 are located at corners of the implant (either with or in the absence of an extension portion). Again, implant 20 is designed for methods that use two opposing implants, one to support each side of the levator muscle. Implant 20 includes two (optional) frames, 21. As illustrated, these are located at edges of long sides of implant 20. Frames 9 are slightly curved to match the shape of the edges. FIG. 2 shows two frames, but more or fewer could be included.

Figure 3:
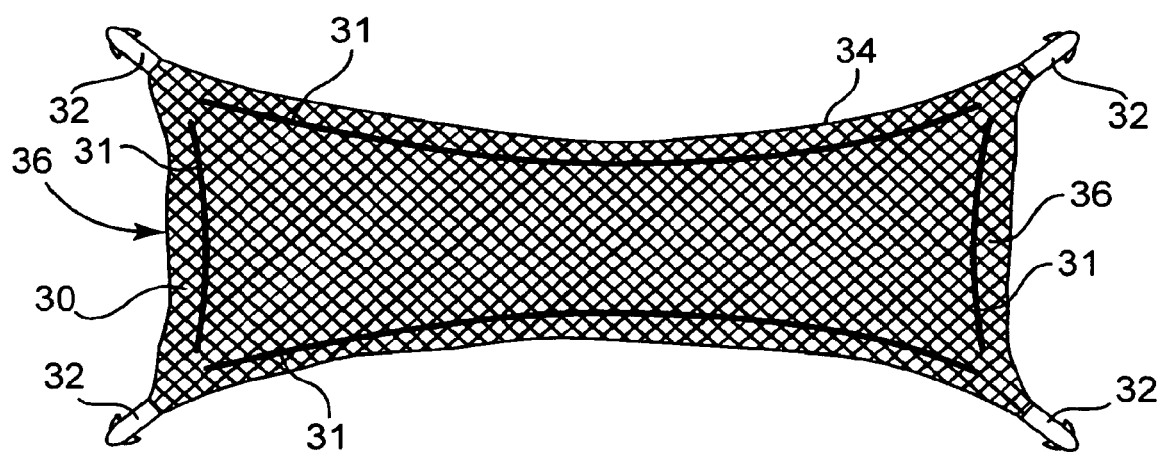
FIG. 3 illustrates an embodiment of an implant as described.

FIG. 3 illustrates an alternate implant, implant 30, which includes two opposing trapezoidally shaped portions of an implant, the opposing portions being connected integrally at the middle by a connection of narrow ends. Implant 30 may be integrally constructed or prepared from two implants of the type shown in FIG. 2. Implant 30 also includes self-fixating tips 32, which, in use, can be placed as described for extension portions 12 of implant 2. In use, narrow medial portion 34 of implant 30 can be placed medially, e.g., under the rectum. Lengths of wide ends 36 can be, e.g., from 4 to 5 centimeters. The width of implant 30 at narrow medial portion 34 can be, e.g., from 2 to 3 centimeters. The total length (the direction perpendicular to with at medial portion 34) can be, e.g., from 14 to 18 centimeters, e.g., from 15 to 17 centimeters.

Implant 30 includes four (optional) frames, 31. As illustrated, these are located at edges of long sides of implant 20.

Frames 31 are slightly curved to match the shape of the edges. FIG. 3 shows four frames, but more or fewer could be included.

Figure 4:
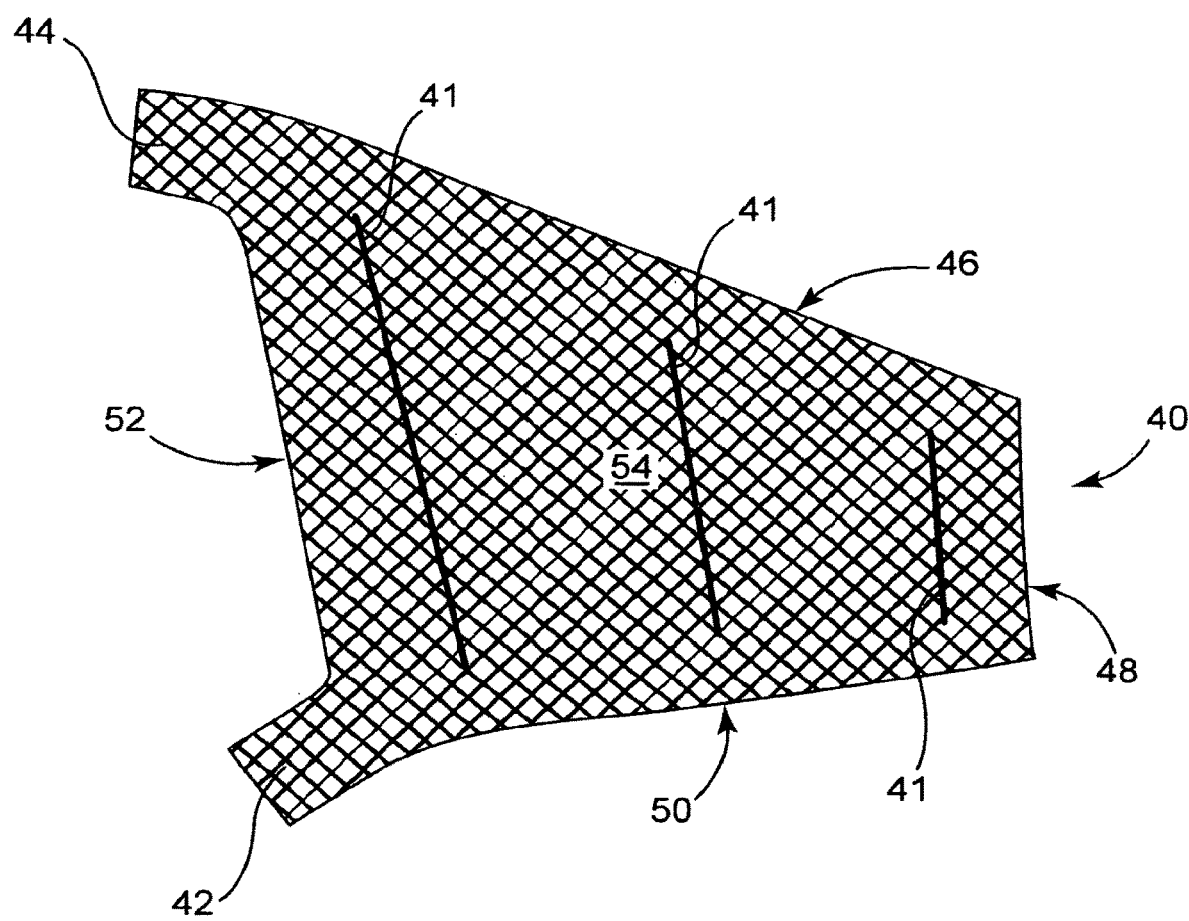
FIG. 4 illustrates an embodiment of an implant as described.

Another embodiment of an implant is shown at FIG. 4. Implant 40, including tissue support portion 54, is generally in the form of a non-symmetric trapezoid. Two extension portions, anterior extension portion 44 and posterior extension portion 42, are located at corners that connect lateral end 52 to anterior side 46 and posterior side 50. Anterior side 46 and posterior side 50 extend medially to medial end 48. Tissue fasteners (not shown) can optionally be placed at extension portions 42 and 44. In use, anterior extension portion 44 can be attached to tissue of the anterior pelvic region, for example tissue of the obturator foramen, e.g., the obturator intern us muscle near the inferior pubic ram us, or at tissue of the arcus tendineus. Posterior extension portion 42 can be attached to tissue of the posterior pelvic region, such as in a region of the ischial spine, e.g., at a sacrospinous ligament, ischiorectal fossa, or iliococcygeous muscle. Lateral side 52 extends anteriorly to posteriorly at a lateral position, and medial end 48 becomes located at a medial position, for example, under the rectum. When so placed the implant extends from lateral positions between, e.g., a region of the ischial spine, and, e.g., a region of the obturator foramen, with tissue support portion 54 in contact with levator tissue, and with medial end 48 at a medial position, e.g., near the rectum, optionally under the anococcygeal body ligament. Overall, the implant can provide lateral support along the iliococcygeus muscle, and more central support along the pubococcygeus and puborectalis.

Implant 40 includes three (optional) frames, 41. As illustrated, these are located generally at surfaces (as opposed to edges) of tissue support portion 54. Frames are substantially straight and generally parallel. Advantageously, implant 40 is capable of being rolled or folded into a configuration that keeps frames 41 in a parallel orientation. In a folded or rolled form, implant 40 is capable of being inserted through a small tissue incision or tissue path. Once placed as desired in a pelvic region of a patient, implant 40 can be unfolded or unrolled and frames 41 can assist in causing implant 40 to be spread out and can maintain a spread out (open) orientation of implant 40. FIG. 4 shows three frames, but more or fewer could be included.

Lengths of the ends and sides can be as desired to allow for this placement. For example, a lateral end 52 can be, e.g., from 5 to 7 centimeters. A length of anterior side 46 can be can be in the range from 5 to 10 centimeters, such as from 6 to 9 centimeters. A length of posterior side 50 can be somewhat shorter, such as from 4 to 8 centimeters, or from 5 to 6 centimeters. Length of medial end 48 can be, e.g., from 2 to 3 centimeters.

In FIG. 4, implant 40 is of synthetic mesh, but can alternately be of a biologic material.

According to methods of the invention, implant 40 can be inserted through a medial incision (e.g., a perineal incision) and placed as described, below tissue of the pelvic floor such as coccygeus muscle or levator muscle. Implant 40 is placed below tissue of one side of the pelvic floor, to support substantially one side or half of the pelvic floor. A second implant of the same design (but in the form of a mirror image) can be placed to support the contralateral side of the pelvic floor, according to the same method. In this embodiment of implant and methods, two separate implants are used, one to support each side of the levator muscle, with medial ends extending to a medial location. Preferably, the implants are also located below the superficial transverse perineal muscle. The medial ends may overlap or be secured, e.g., by a suture or other securing means such as adhesive, staples, etc. In an alternate embodiment, two implants, 40, and a mirror image, can be connected at medial ends and used as a single implant.

One or more insertion tool can be used to install an implant. Various types of insertion tools are known, and these types of tools and modifications thereof can be used according to this description to install an implant. Examples of useful tools include those types of tools that generally includes a thin elongate shaft or needle that attaches to a handle; a handle attached to one end (a proximal end) of the needle or shaft; and a distal end of the needle adapted to engage an implant.

According to one embodiment of a tool, a distal end of a needle can engage a self-fixating tip of an implant. The needle can push the self-fixating tip through a tissue passage and insert the self-fixating tip within tissue of the pelvic region. (In alternate embodiments, a connector can be used in place of the self-fixating tip, the connector being able to engage a distal end of an insertion tool to allow the connector to be pushed or pulled through a tissue path leading to an external tissue incision.) This class of tool can be used with a self-fixating tip (or other form of connector) that includes an internal channel designed to be engaged by a distal end of an insertion tool.

Other general types of insertion tools will also be useful for engaging a self-fixating tip, but may engage the self-fixating tip (or connector) in a manner that does not involve an internal channel of a self-fixating tip. These alternate insertion tools may for example contact or grasp a proximal base end of a self-fixating tip in the absence of an internal channel extending from the proximal base end toward the distal base end, such as by grasping an external surface of the base. An alternate insertion tool may contact or grasp a side of the base, a lateral extension, or any other portion of the self-fixating tip or base, in a way that allows the insertion tool to hold the self-fixating tip and insert the self-fixating tip at a desired location within tissue of the pelvic region.

Exemplary insertion tools for treatment of incontinence and vaginal prolapse are described, e.g., in United States patent application Ser. Nos. 10/834,943, 10/306,179; 11/347,553; 11/398,368; 10/840,646; PCT application number PCT/US2006/028828; and U.S. application number US-2006-0260618; among others. Tools described in those patent documents are designed for placement of an implant in a pelvic region for the treatment of prolapse, male or female incontinence, etc. The tools of the above-referenced patent documents may be straight or may be curved in two or three dimensions, and may include, for example, a helical portion in three dimensions for placing an extension portion of an implant through a tissue path that passes from a region of the urethra, through an obturator foramen, to an external incision in the groin or inner thigh area. Other described insertion tools include a two or three-dimensional elongate needle that allows a user to place an extension portion of an implant through an external incision, e.g., at a suprapubic location or at a perianal or perirectal location.

Exemplary insertion tools for use can be similar to or can include features of tools described in the above-referenced patent documents. For use according to embodiments of methods described herein, wherein an implant includes a self-fixating tip, those insertion tools may be modified to allow the insertion tool to be used to place a self-fixating tip at tissue within the pelvic region through a tissue path that does not extend to an external incision. The insertion tool can be designed, shaped, and sized, to include an elongate inserter or needle that may be straight or that may be curved in two or three dimensions, that can be inserted through a vaginal incision (for female anatomy), through a perineal incision (for male anatomy), or through any one of the other incisions described herein, and to extend from that incision to a pelvic tissue location for placement of a self-fixating tip. Certain embodiments of insertion tools can be designed to reach through a vaginal incision, perineal incision, or other described incision, through an internal tissue path, and to then extend through a second (external) incision, e.g., at the inner groin, thigh, abdominal area, suprapubic region, or perirectal or perianal region. Alternate tools can be sized and shaped to place a self-fixating tip at an internal location of the pelvic region, and do not need to be sufficiently long to extend from an incision to an external incision. The length can be only sufficient to reach from a vaginal or perirectal incision to an obturator foramen, region of the ischial spine, sacrospinous ligament, or other location of placing a self-fixating tip. Alternately, the length may be only sufficient to reach from a desired incision to a different muscle or tissue, such as a levator ani, coccygeous muscle, iliococcygeous muscle, arcus tendineus, etc., to place a self-fixating tip at one of those tissues.

Another tool that can be useful with an implant can be a tool that includes a spreader at a distal end (i.e., a "spreader tool"). A spreader tool can be used for placing an implant, in which instance a spreader tool is also an insertion tool; a spreader tool may be used to pass an implant through an incision, place the implant at a desired location, and then spread the implant. Alternately, a spreader tool may be used separately from or in combination with a different tool, e.g., a different insertion tool, such as an insertion tool that includes an elongate needle that engages a self-fixating tip and allows placement of the self-fixating tip. For example, an insertion tool may be used to place an implant at a desired location within a pelvic region, the insertion tool may be removed, then the spreader tool may be inserted into the pelvic region to be used to spread the implant.

A spreader tool can include a handle, shaft, and a distal end that includes a "spreader" that engages an implant to spread the implant to an open (e.g., unfolded) state. The shaft can be elongated, and of a length that allows the handle to be held and manipulated outside of a patient, while the distal end functions at a location internal to the patient. The distal end can be of a reduced cross-sectional profile to allow the distal end to be inserted through an external or vaginal incision.

The spreader can include at least one moveable portion that can be moved, bent, or non-permanently deformed, to cause or allow implant material that is engaged with the spreader to become spread to an open form. An example of a spreader can be a set of opposing jaws, each capable of engaging material of the implant, and one or both of which can be moved relative to the shaft to open the jaws. Implant material can engage each jaw in any fashion. When the jaws are spread apart to a spread position the implant material becomes spread apart to expose the surface of the implant. Another example of a spreader can be a rigid yet flexible and deformable plastic or metal frame that is biased to a spread position, that can become un-spread (e.g., folded or collapsed), and then re-spread. The wire frame may engage an implant and then be allowed or caused to spread apart (i.e., open), thereby spreading the implant material to an opened shape.

Figure 11:
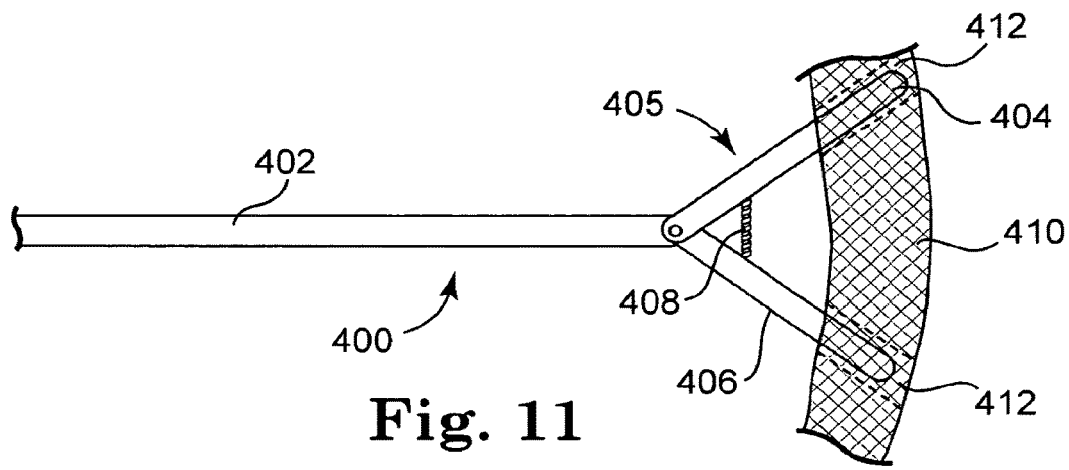
FIGS. 11, 12, 13A, 13B, and 14 illustrate embodiments of implants and spreader tools.

FIG. 11 shows an example of a spreading tool that includes a spreader at a distal end of the shaft. Tool 400 includes shaft 402 and spreader 405 at a distal end of shaft 402. Spreader 405 includes opposing jaws 404 and 406, each being moveable relative to each other and relative to shaft 402. Each of jaws 404 and 406 engages implant 410 at bearings (pockets) 412, which are sewn or woven into implant 410. Spring 408 is biased open, but jaws 404 and 406 can be closed by a closing mechanism (not shown), that is operable from a handle (not shown) located at a proximal end of shaft 402. When jaws 404 and 406 are closed, spreader 405 can has a small cross-sectional profile (which is the area of the closed jaws when viewed along their longitudinal axis) and can be passed through a small incision such as a vaginal or external incision, then through a tissue path extending to a location within a pelvic region of a patient. Once the spreader is placed as desired, opposing jaws 404 and 406 can be spread apart and implant 410 can be caused to be opened to a flat, unfolded orientation for implantation.

Figure 12:
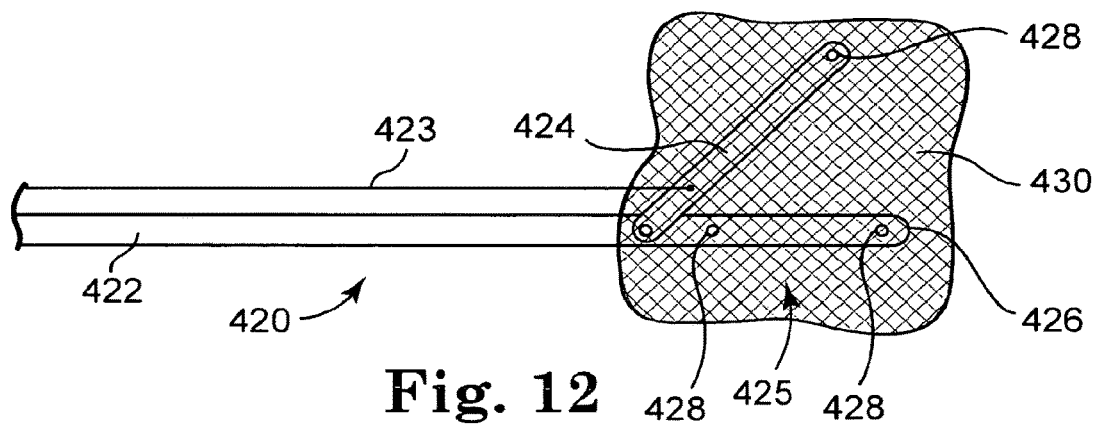

FIG. 12 shows another example of a spreading tool. Tool 420 includes shaft 422 and spreader 425 at a distal end of shaft 422, spreader 425 including opposing jaws 424 and 426, jaw 424 being moveable relative to jaw 426 (which is stationary) and to shaft 422. Actuator 423 is connected to moveable jaw 424, and also to an actuator at a handle (not shown) located at a proximal end of shaft 422. Each of jaws 424 and 426 engages implant 430 at retractable pins 428. Retractable pins 428 are sized to engage apertures of implant 430, which may be a mesh or other aperture-containing material such as a film of woven or non-woven sheet. Pins 428 can be retracted by a retracting mechanism (not shown) that can be actuated at a handle (not shown) located at a proximal end of shaft 422. When jaws 424 and 426 are closed, spreader 425 exhibits a small cross-sectional profile (which is the area of the closed jaws when viewed along their longitudinal axis) and can be passed through a small incision such as a vaginal or external incision, then through a tissue path extending to a location within a pelvic region of a patient. This can preferably be done while spreader 425 is engaged with implant 430. Once spreader 425 is placed as desired, and while engaged to implant material 430, opposing jaws 424 and 426 can be spread apart and implant 430 can be caused to be opened to a flat, unfolded orientation for implantation.

Figure 13A:
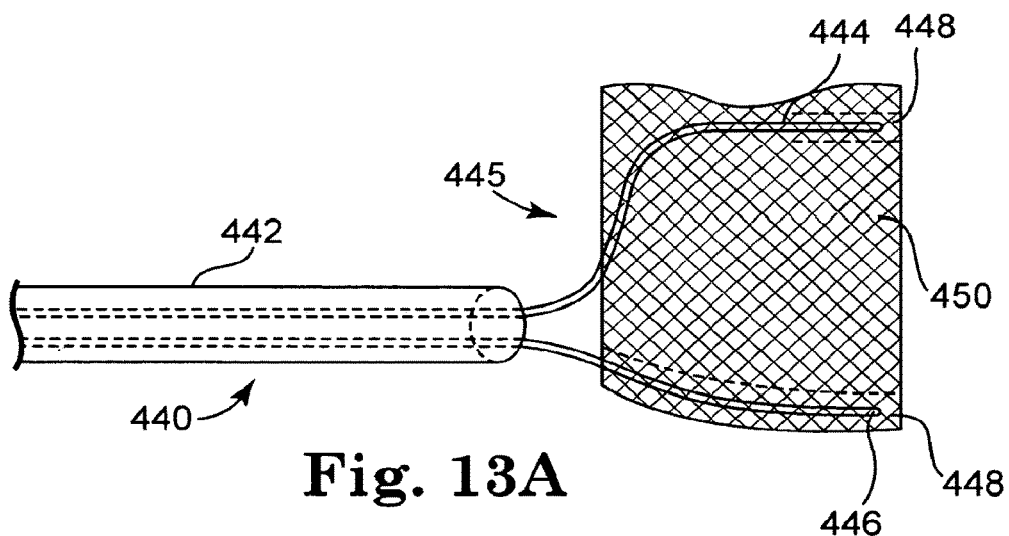
Figure 13B:
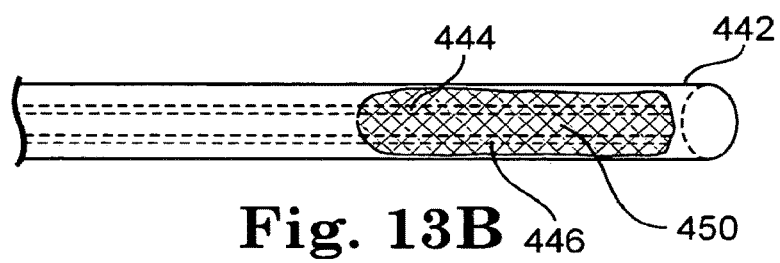

FIGS. 13A and 13B illustrate another example of a spreading tool. Tool 440 includes shaft 442 in the form of a hollow and elongate tube, cannula, or "trocar," and spreader 445 at a distal end of shaft 442. Spreader 445 includes opposing jaws 444 and 446. These jaws, 444 and 446, are biased to an opened position as shown at FIG. 13A. The jaws can be made of metal (e.g., spring steel, nitinol, etc.) or plastic that exhibit flexibility, resiliency, and shape-memory, resulting in an ability to become opened and then to collapse when extended from and drawn back into the channel defined by shaft 442. At a proximal end of shaft 442 is a mechanism that allows jaw 444 and 446, independently or together, to be retracted into or extended from shaft 442. Each of jaws 444 and 446 engages implant 450 at bearings (pockets) 448 formed into implant material 450.

Referring to FIG. 13B, this illustrates jaws 444 and 446 being in an uni-opened position retracted within shaft 442. To achieve this configuration, jaws 444 and 446 are placed together, implant 450 is folded or wound around the jaws, and the assembly is withdrawn into shaft 442. In this configuration, the assembly of shaft 442, with retracted jaws and folded implant 450, can be passed through a small incision such as a vaginal or external incision, then through a tissue path extending to a location within a pelvic region of a patient. Once the distal end of shaft 442 is placed as desired, jaws 444 and 446 can be extended from the distal end of shaft 442, whereupon they will open to unfolded relatively flat configuration shown at FIG. 13A, for placement within a patient's pelvic region.

Figure 14:
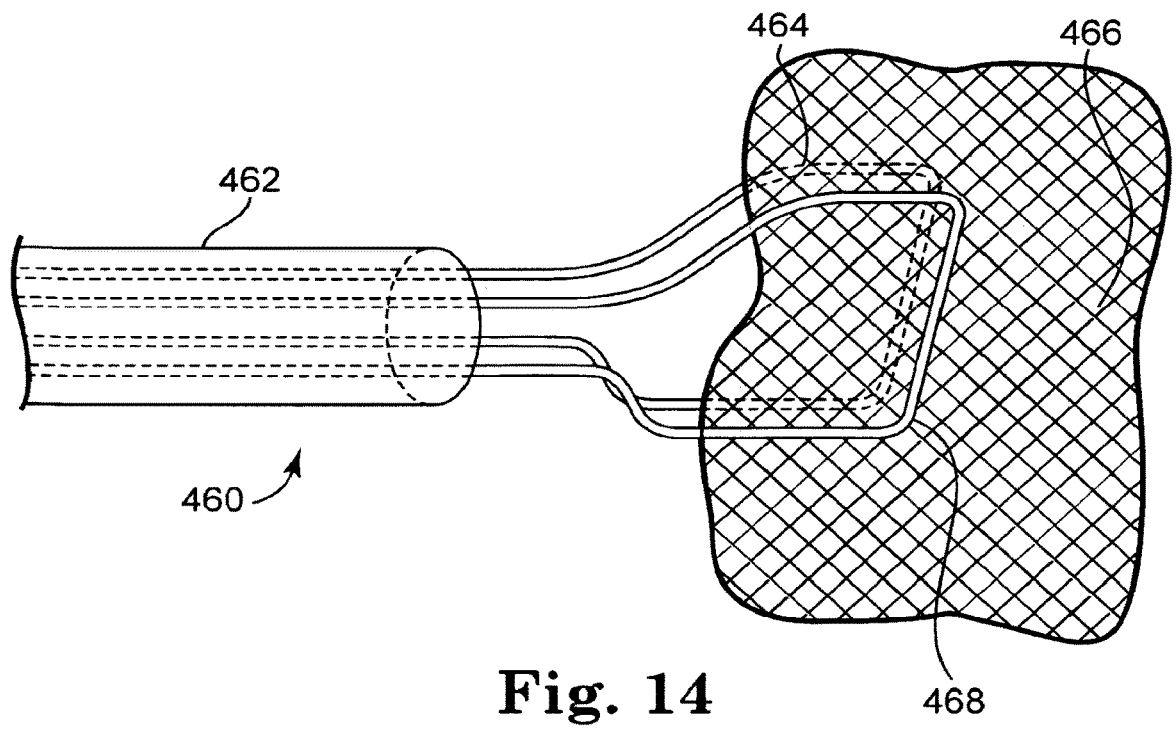

FIG. 14 and illustrate another example of a spreading tool. In this embodiment, the spreader can engage the implant in a manner that does not require the implant to include a bearing designed to fit a feature of the implant. Instead, the spreader portion of the spreader tool includes two opposing spreaders that can press together to engage the implant. The spreaders are biased to exhibit a spread configuration when extending from the shaft of the spreader tool, and are sufficiently flexible to become bent (without resulting in permanent deformation) when retracted into a hollow shaft of the spreader tool.

Referring to FIG. 14, spreader tool 460 includes shaft 462 in the form of a hollow and elongate tube, cannula, or "trocar," and spreaders 464 and 468 at a distal end of shaft 442. Spreader 464 and 468 are biased to an opened (spread) position as shown at FIG. 14, when extended from shaft 462. The spreaders 464 and 468 can be made of a flexible material such as metal (e.g., spring steel, nitinol, etc.) or plastic that exhibit flexibility, resiliency, and shape-memory, resulting in an ability to become spread and then to collapsed (unspread) when extended from and drawn back into, respectively, the hollow internal channel defined by shaft 462. Spreaders 464 and 468 are also biased to press toward each other to allow an implant material to be grasped between the opposing spreaders. At a proximal end of shaft 462 are mechanisms that allow spreaders 464 and 468, independently or together, to be retracted into or extended from shaft 462.

In use, spreaders 464 and 468 engage implant 466 by pressing together to hold implant 466 between spreader 464 and 468. The implant is not required to have bearings. FIG. 14 illustrates implant 466 being in an spread (open) configuration, held between spreaders 464 and 468, which are extended from shaft 462. In an alternate configuration, spreaders 464 and 468, grasping implant 466, can be retracted into shaft 462; spreaders become unspread and a portion of implant 466 that is grasped by spreaders 464 and 468 is retracted into shaft 462 and becomes folded (unspread). In a retracted configuration, the assembly of shaft 462, with retracted (and unspread) spreaders and implant 466, can be passed through a small incision such as a vaginal or external incision, then through a tissue path extending to a location within a pelvic region of a patient. Once the distal end of shaft 462 is placed as desired, spreaders 464 and 468 can be extended from the distal end of shaft 462, whereupon they will open to an unfolded relatively flat configuration as shown at FIG. 14, for placement of implant 466 within a patient's pelvic region. Once the assembly is placed, spreaders 464 and 468 can be withdrawn independently, one first then the second, to leave the mesh at an intended location of implantation.

Figure 15A:
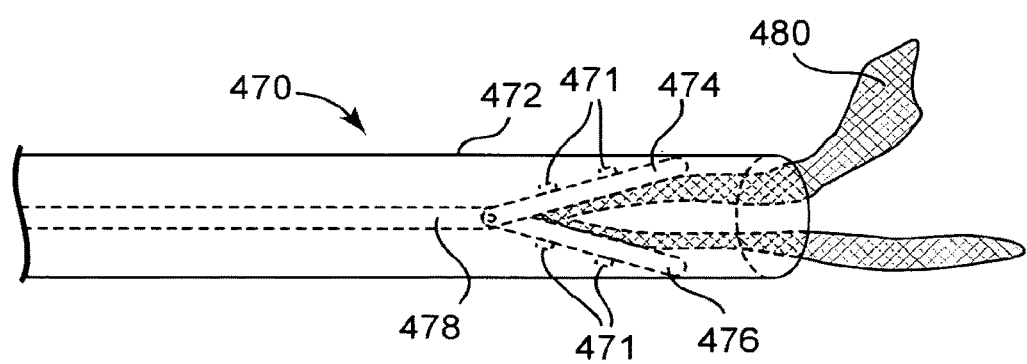
FIGS. 15A and 15B illustrate embodiments of implants and spreader tools.
Figure 15B:
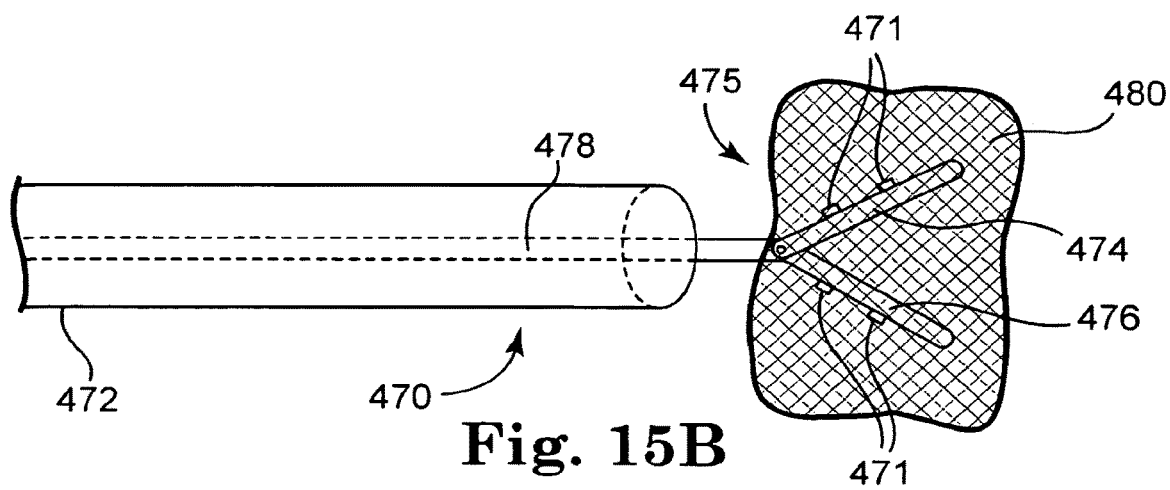

FIGS. 15A and 15B illustrate another example of a spreading tool. Tool 470 includes shaft 472 in the form of a hollow and elongate tube, cannula, or "trocar," and spreader 475 at a distal end of shaft 472. Spreader 475 includes opposing jaws 474 and 476. These jaws are biased to an opened position as shown at FIG. 15B. The jaws can be made of metal (e.g., spring steel, nitinol, etc.) or plastic and may be hinged at their connection to extended 478, so that the opposing jaws can become opened and then closed when extended from and withdrawn back into the channel defined by shaft 472. At a proximal end of shaft 472 is a mechanism connected to extender 478 spreader 475 to be retracted into or extended from shaft 472. Each of jaws 474 and 476 engages implant 480 at pins 471.

Referring to FIG. 15A, this illustrates jaws 474 and 476 being in an uni-opened (unspread) position retracted within shaft 472. In this configuration, the assembly of shaft 472, with retracted jaws and folded implant 480, can be passed through a small incision such as a vaginal or external incision, then through a tissue path extending to a location within a pelvic region of a patient. Once the distal end of shaft 472 is placed as desired, jaws 474 and 476 can be extended from the distal end of shaft 472, whereupon they will open and cause implant 480 to open to an unfolded relatively flat configuration shown at FIG. 15B, for placement within a patient's pelvic region.

Optionally, an implant can include one or multiple self-fixating tips at a tissue support portion or optionally at one or multiple ends of optional extension portions, and an implantation method can include placing the self-fixating tip or tips within tissue in the pelvic region to support the implant as the implant supports a type of pelvic tissue. The tissue can be a fibrous tissue such as a muscle (e.g., of the obturator foramen, obturator internus, obturator externus, levator ani, coccygeous, iliococcygeous), ligament (e.g., sacrospinous ligament), tendon (arcus tendineus), etc. Also preferably, but not as a requirement of the invention, a self-fixating tip can be oriented in a fibrous tissue to cause a major dimension (referred to herein as the "width") of a lateral extension to be oriented in a direction that is not parallel to the direction of the fibers.

To control the placement and degree of support of the implant relative to a tissue to be supported by the implant, the self-fixating tip can be inserted at a desired point of entry relative to the total area of the tissue, and, for tissues of sufficient thickness or depth, the self-fixating tip can be inserted to a selected depth.

A single example of a method according to the invention is a method of improving positioning of, or supporting, tissue of the pelvic floor or a portion thereof, by surgical implantation of an implant (e.g., a single, integral, optionally uniform, woven polymeric mesh strip) through an incision that allows access to the tissue of the pelvic floor (e.g., levator tissue, coccygeus tissue), such as a vaginal incision (for female anatomy), perineal (for male or female anatomy) incision, or another incision as described herein. Certain embodiments of these methods can advantageously involve only a single incision (a vaginal incision in a female or a perineal incision in a female or male) and can exclude the need for any additional incision.

Figure 5A:
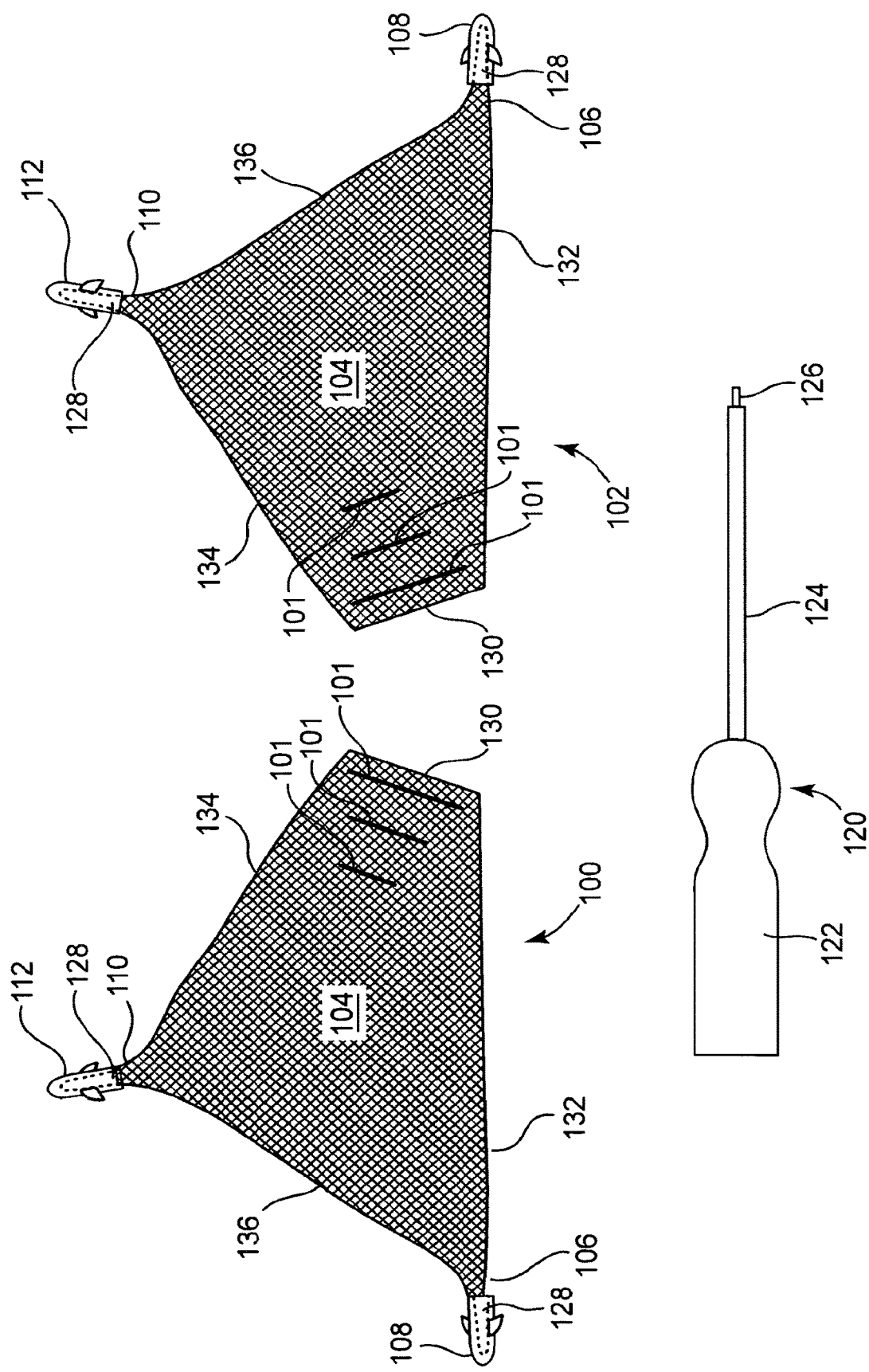
FIG. 5A illustrates an embodiment of a kit comprising an implant as described and an insertion tool.

An embodiment of a kit according to the invention, including an insertion tool and an implant, is shown at FIG. 5A. Implant 100 can be installed to support tissue of the levator. Implant 100 is designed to support a portion of levator tissue, and implant 102 is designed to support a contralateral portion of levator tissue. Each implant includes a tissue support portion (104), an anterior extension portion (106) that includes a tissue fastener (108) in the form of a self-fixating tip. Each implant also includes a posterior extension portion (110) that includes a tissue fastener (112) in the form of a self-fixating tip. Sides and ends include: lateral ends 136, which can extend along a lateral portion of the levator, such as near the arcus tendineus between an anterior position and a posterior position; anterior sides 132 extending from medial end 130 to anterior extension portion 106; posterior sides 134 extending from medial end 130 to posterior extension portion 110; and medial end 130.

Implants 100 and 102 each include three (optional) frames, 101. As illustrated, these are located in parallel orientations with medial ends 130.

Tool 120 is also part of the kit. Tool 120 includes handle 122 connected to a proximal end of elongate needle 124. Distal end 126 is configured to engage internal channels or bores 128 (shown in dashed lines) of each of the tissue fasteners 108 and 112. Tool 120 is shown to have a straight needle portion 124, but could have a needle portion that is curved in two or three dimensions.

FIG. 5A shows two implants, 102 and 100, which are mirror images of each other in the form of non-symmetric trapezoids, as part of a kit. Alternate kits could include two implants of other shapes, e.g., as discussed herein, including a rectangle, symmetric trapezoid, square, or any of these general shapes, alternately with one or more of the straight edges being arcuate if desired.

Figure 5B:
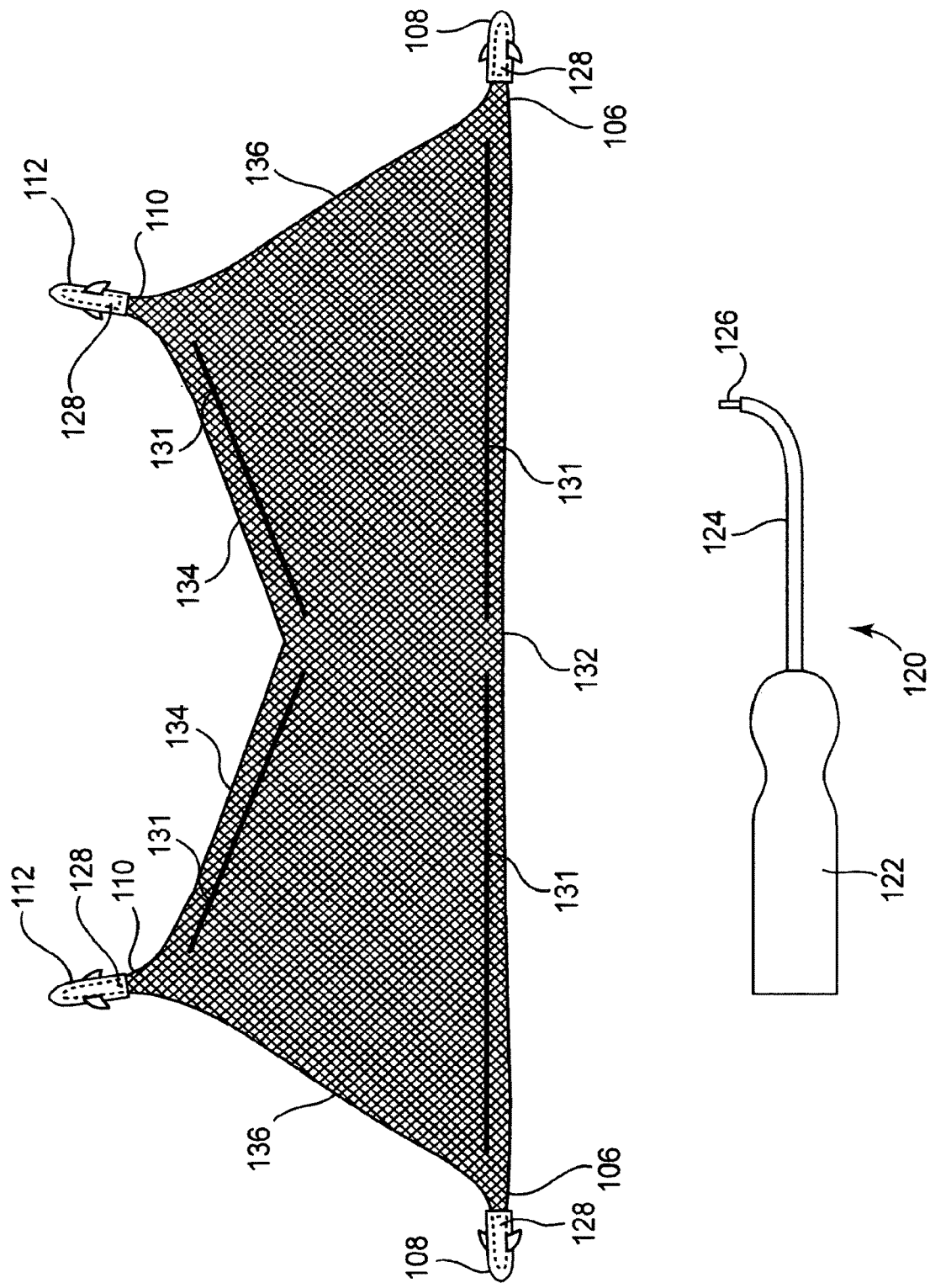
FIG. 5B illustrates an embodiment of a kit comprising an implant as described and an insertion tool.

In other alternate kits, an implant can be in the form generally of the two implants connected (e.g., integrally or by a connection mechanism such as a suture) at medial ends 130. See FIG. 5B. In FIG. 5B, frames 131 are located along sides 132 and 132, to provide shape control of the implant along edges of these sides.

Optionally, according to various implant embodiments, such as implant 100 or 102, a material that forms any portion of a sling 100 may include one or more substances incorporated into the material or coated onto the material of the sling.

Examples of substances may include, without limitation, drugs, hormones, antibiotics, antimicrobial substances, dyes, silicone elastomers, polyurethanes, radiopaque filaments or substances, position or length indicators, antibacterial substances, chemicals or agents, including any combinations thereof. A substance or material may be used to enhance treatment effects, reduce potential sling rejection by the body, reduce the chances of tissue erosion, allow or enhance visualization or location monitoring, indicate proper sling orientation, resist infection, or other provide other desired, useful, or advantageous effects.

Also with respect to any implant, such as implants 100, 102, or alternate embodiments, sling tension may be adjusted by a tension member such as a tensioning suture disclosed, for example, in U.S. Pat. No. 6,652,450. The tensioning suture may be constructed from a permanent or absorbable (i.e., bioresorbable or bioabsorbable) material. The tensioning member may be located along any portion of the implant such as a tissue support portion or extension portion.

Certain embodiments of the present invention are described with reference to supporting levator tissue and coccygeus tissue. Additionally, the invention is also useful for more specifically treating symptoms caused by weakened or damaged levator or coccygeus tissue, in both males and females. For example, embodiments of the present invention would be suitable for a variety of pelvic floor repairs or treatments, including pelvic organ prolapse repair, levator ballooning, a paravaginal defect such as levator avulsion, levator hiatus repair, fecal incontinence treatment, perineal body support, rectal support, levator tissue repair, etc.

Figure 6:
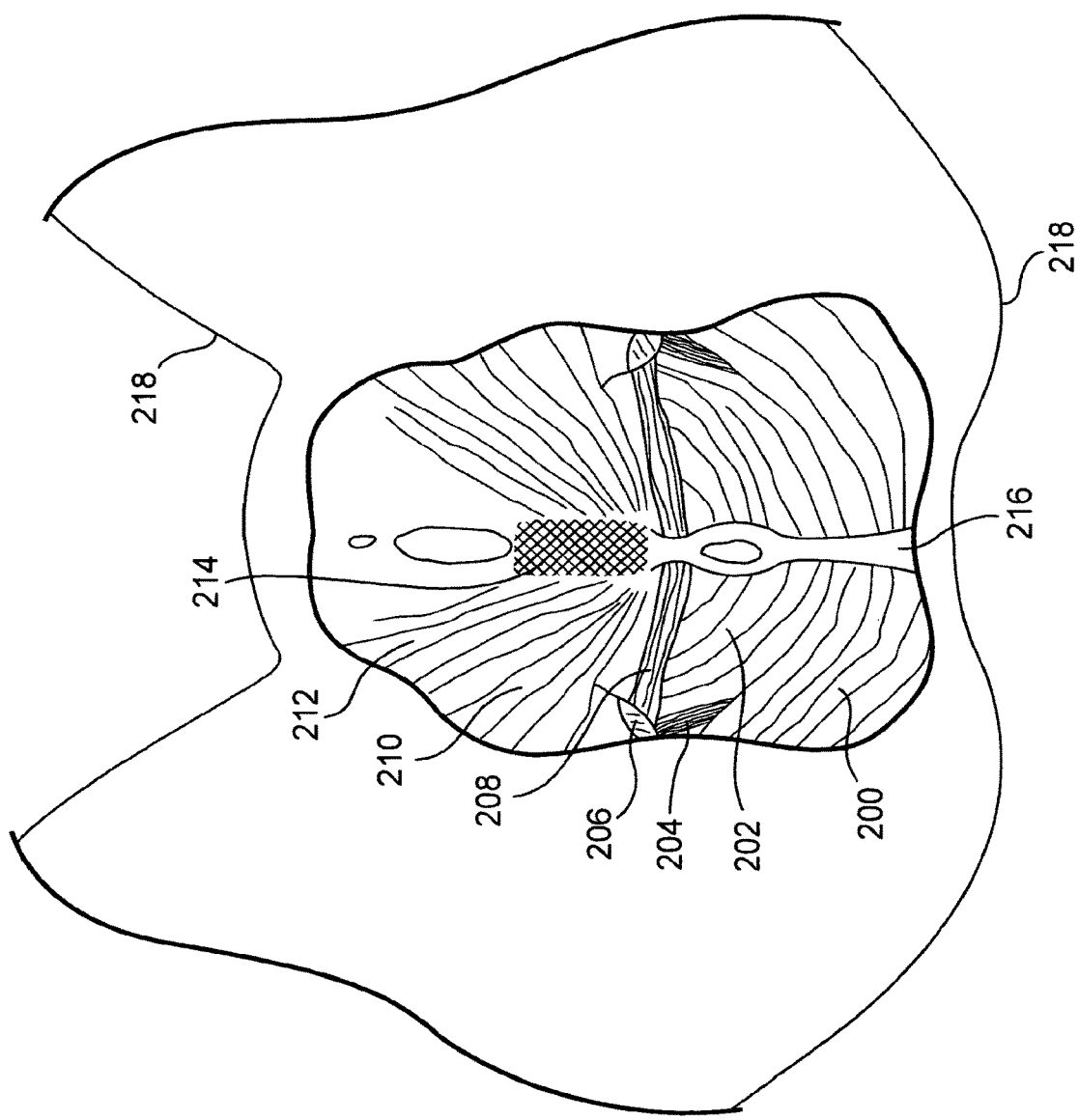
FIG. 6 illustrates anatomy of the pelvic region.

FIG. 6 shows anatomy relevant to methods and devices of embodiments of the invention. Referring to FIG. 6, illustrated is an view of inferior tissue at different levels of the pelvic region, including gluteus maximus 200, levator ani 202 (which includes the iliococcygeus muscle), sacrotuberous ligament 204, ischial tuberosity 206, superficial transverse perineal muscle 208, pubococcygeus muscle 210, puborectalis muscle 212, and perineal body 214. Epidermis 218 and coccyx 216 are shown for reference.

According to exemplary methods of the invention, a method of supporting levator or coccygeus tissue can include a step of creating an incision that allows access to a region of lower (inferior) levator or coccygeus tissue. Upon making the incision, some amount of dissection may be preferred or necessary. For example, placement of an implant may be performed with dissection of a plane or region of dissection that includes the ischorectal fossa. Anatomical landmarks included with this region of dissection can include the ischial spine, the obturator internus, the arcus tendineus.

An implant or a portion of an implant can be inserted through the incision or accessed through the incision. The implant can be as generally or specifically described herein, such as in any of FIGS. 1 through 4, 5A, and 5B, including a tissue support portion, and optionally including one or multiple tissue fasteners optionally located at a corner of an implant or at a distal end of an optional extension portion. The implant can be passed through the incision and the tissue support portion is placed to support levator tissue, coccygeus tissue, or both, at an inferior region or inferior side thereof (i.e., "below" or inferior to tissue).

According to certain embodiments of the invention, the tissue support portion can also be located below (inferior to) the superficial transverse perineal muscle, to support this tissue as well. The tissue support portion can optionally be secured to levator tissue, tissue of the superficial transverse perineal muscle, or both. The tissue support portion is positioned at a region of inferior levator tissue in a manner to cause the tissue support portion to support levator tissue. Optionally the tissue support portion can be positioned below the rectum, attached to the rectum, or attached to the external anal sphincter.

Referring to FIG. 6, an embodiment of a method can include placing the implant, e.g., the tissue support portion or a distal end of an extension portion, into contact with supportive tissue selected from: sacrotuberous ligament, periostium of the pubic bone (not shown in FIG. 6), pubourethral ligament (also not shown, but connects urethra to pubic bone), arcus tendineus (not shown), anococcygeal body ligament (not specifically shown), sacrospinous ligament (not shown in FIG. 6), a region of the ischial spine, or ischial tuberosity. Alternately or additionally, the tissue support portion or an extension portion can be attached to periostium of the pubic bone in a region of the ischial tuberosity. Alternately or additionally, a tissue support portion or extension portion can be extended through a tissue path between levator ani muscle and obturator internus muscle and attached at the arcus tendineus (white line), at the obturator membrane, or extend through the obturator foramen to an external incision at the inner thigh.

In general for a fecal incontinence sling and other pelvic floor and levator ani muscle repairs, anchoring points for a tissue fastener such as a self-fixating tip or a bone anchor could include sacrotuberous ligament laterally or the periostium of the pubic bone—specifically by the ischial tuberosity. Additionally, a bone anchor could be placed at the ischial tuberosity to attach the sling internally at the pelvic region. The sling can pass under the external anal sphincter and be attached laterally at each side (e.g., at the ischial tuberosity). According to one specific embodiment, the sling could be placed using self-fixating tips. In addition, the sling and self-fixating tips could be placed between the levator ani muscle and the obturator internus muscle, attaching the fascia) white line or "arcus tendineus." Optionally and preferably the sling could be placed directly over the superficial transverse perineal muscle, adding the foundational support of the pelvic floor.

In this embodiment, while wishing to not be bound by theory, it is believed that the sling will not only function to restore the anal rectal angle but will also or alternately provide a backstop for the levator muscles. This will allow the anus more support for closure and maintenance of continence. Restoring the anchoring point of the levator ani muscles allows them to contract more efficiently to close off the anal canal.

Alternately or in addition, the sling can be attached to the puborurethral ligament, which may restore the rectal angle. Curing fecal incontinence in this manner is at least in part due to restoring the leverage points for the levator plate and longitudinal muscle of the anus, in addition to any improvement due to restoring the anal rectal angle.

Yet another possible placement for a tissue fastener can be the sacrum, e.g., using a bone anchor, or at the sacrospinous ligament or anococcygeal body ligament, by attaching a tissue fastener.

According to still further embodiments, an extension portion of an implant can pass through a tissue path in the pelvic region to an external incision, such as: through a tissue path that extends to an external incision in at the abdomen; through a tissue path that extends above the pubic bone to a suprapubic incision; through a tissue path that extends through an obturator foramen and to an external incision at the inner thigh; through a tissue path that extends laterally through a region of the coccyx to an external incision adjacent to the coccyx; or through a tissue path that extends to an external incision at a perirectal or perianal region.

As is apparent from the present description, an implant can be installed by any one or combination of incisions that can result in direct access to the pelvic region, to support tissue such as vaginal tissue, urethra or bladder tissue, tissue of the pelvic floor, etc. Generally, incisions and tissue path can be of the types referred to as transvaginal, transobturator, suprapubic, transperineal, transrectal, or retropubic exposures or pathways.

Examples include a perirectal incision that allows open access to tissue of the pelvic floor; a small external perirectal incision that can allow a tissue path to extend from the external perirectal incision to tissue of the pelvic floor; a small external incision in a region of the coccyx that can allow a tissue path to extend from the external incision to tissue of the pelvic floor; a suprapubic incision that involves a small or large external incision at the suprapubic position; a transobturator approach whereby an extension portion of an implant can be placed through a tissue path leading from an external incision at the inner thigh, through an obturator, and to an implant located to support tissue of the pelvic floor; the use of a Kraske incision, e.g., an incision under the rectum; a "modified Kraske" incision; a perineal incision; and a vaginal incision. Certain useful methods can involve reduced need for external incisions based on the use of internal tissue fasteners such as self-fixating tips, to fasten the implant to internal tissue of the pelvic region and eliminate the need for exit points of extension portions.

According to one exemplary tissue path, the transobturator tissue path, extension portion of an implant can extend from a tissue support portion at the levator tissue, through a superior aspect of the obturator foreman. Passage through the superior aspect—very top of the obturator foramen—may result in support such as would be provided by the pubococcygeal ligament, and tightening of the levator hiatus, which can repair the perineal body and restore the anorectal angle. Generally, transobturator tissue approaches are described at pending application Ser. No. 11/347,047 "Transobturator Methods for Installing Sling to Treat Incontinence, and Related Devices," filed Feb. 3, 2006, and at US publication 2005/0143618 (Ser. No. 11/064,875) filed Feb. 24, 2005, the entireties of these being incorporated herein by reference.

Figure 7:
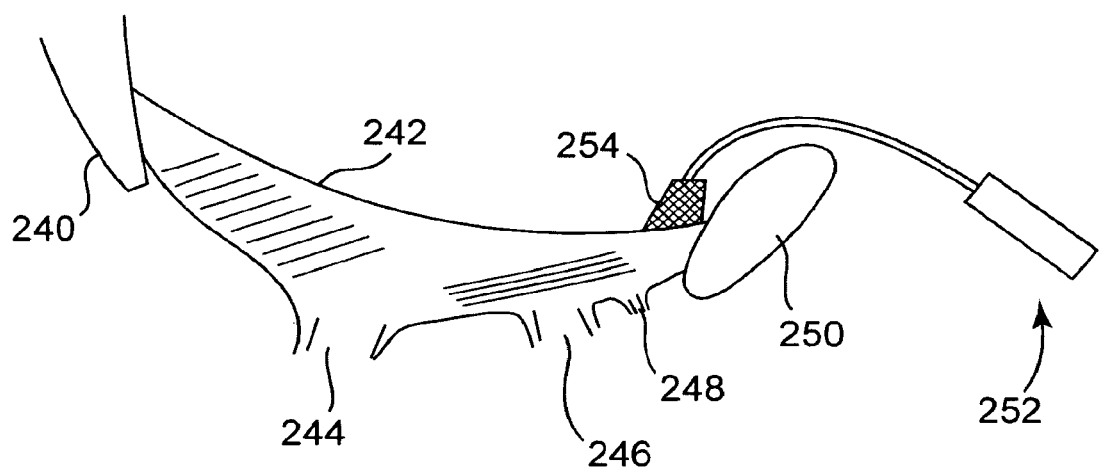
FIG. 7 illustrates an embodiment of tissue path as described.

An example of a suprapubic approach (external incision approach) is illustrated at FIG. 7. Referring to FIG. 7, relevant anatomy includes coccyx 240, white line 242, rectum 244, vagina 246, urethra 248, and pubic bone 250. Insertion tool 252 includes a needle connected to implant 254. A portion (not shown) of implant 254 is located to contact levator tissue and support levator tissue, and a portion (illustrated) such as an extension portion, optionally including a connector for engaging the end of the needle, connects to the needle and is pulled through a tissue path leading from the levator to an external incision in the suprapubic region.

In general, an incision that is in a region of the perineum can be an incision at that location, e.g., between a vagina and an anus in a female. An incision in the perirectal region can be, for example, within 1 to 4 centimeters of the anus.

Figure 8A:
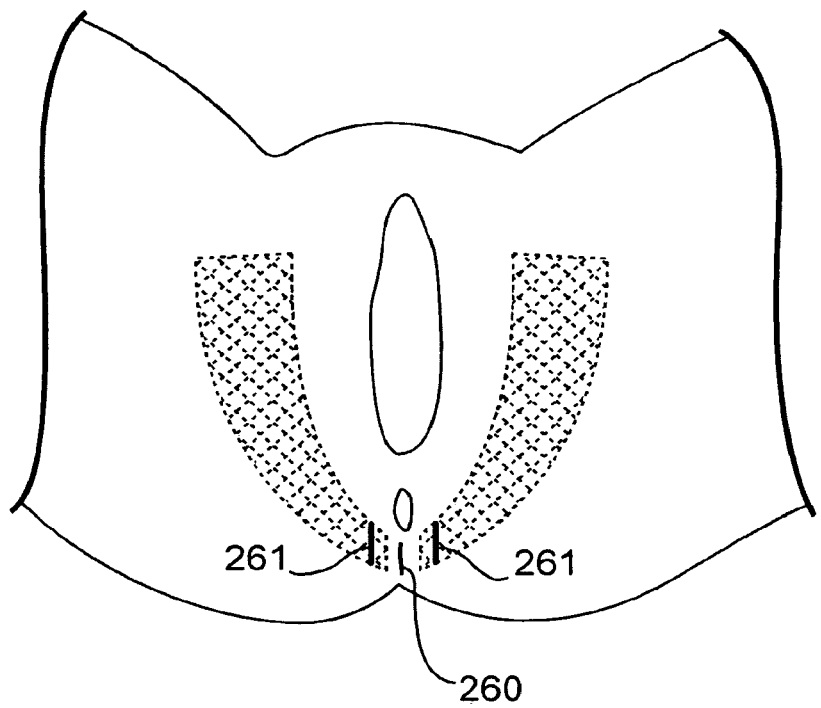
FIGS. 8A, 8B, 8C, and 8D illustrate embodiments of incisions as described.
Figure 8B:
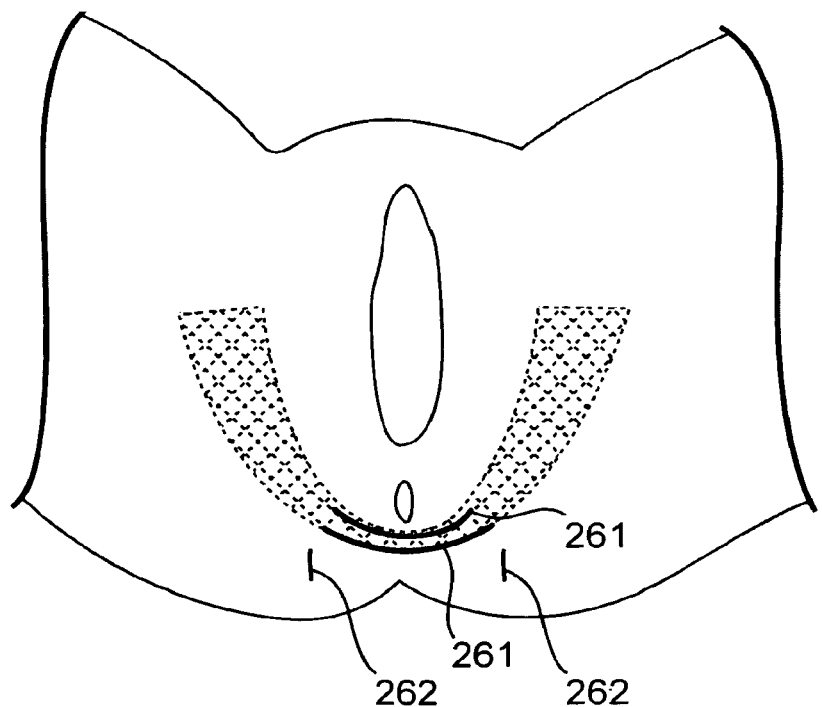
Figure 8C:
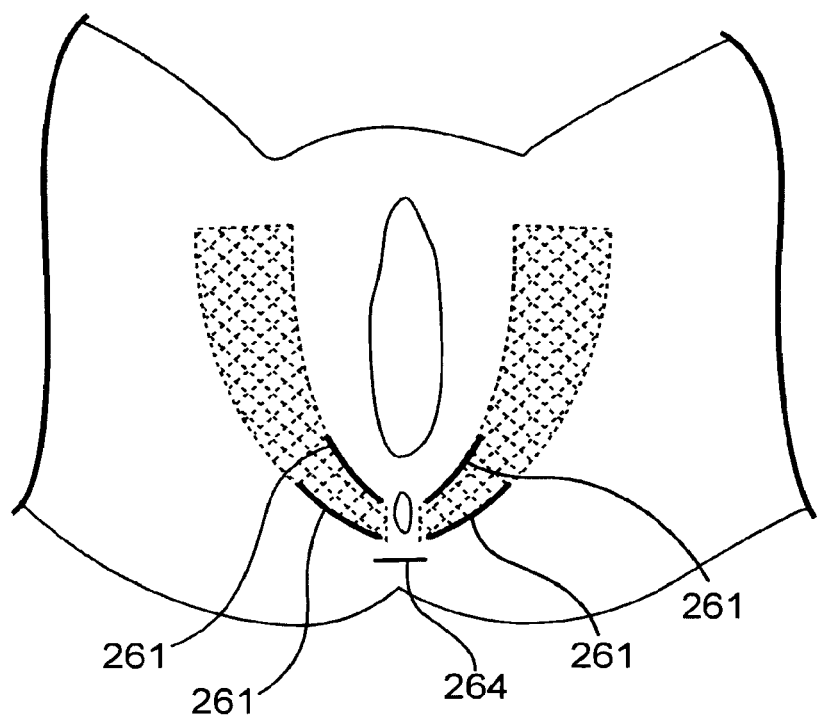
Figure 8D:
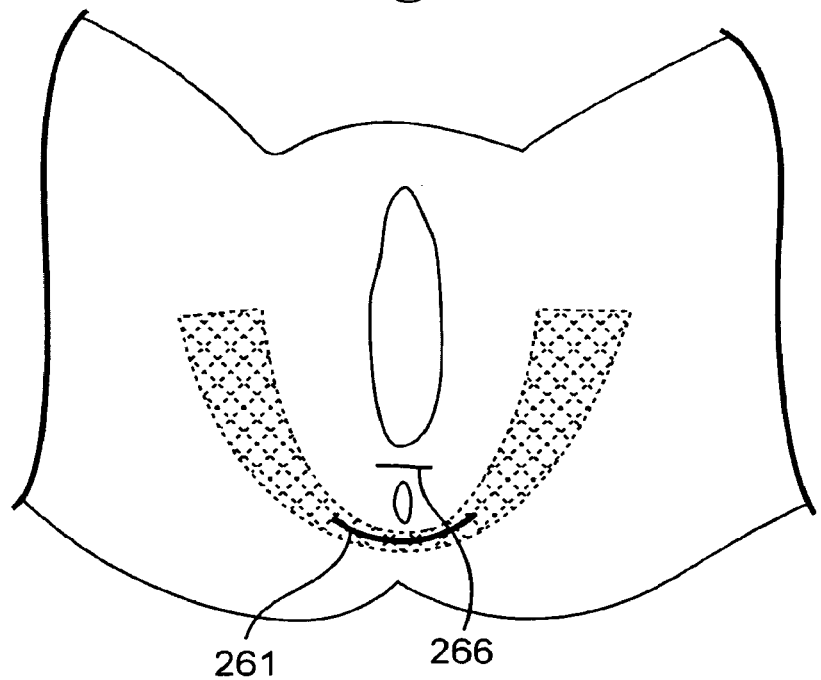

An example of a "modified" Kraske incision (260) (modified to a vertical orientation) is illustrated at FIG. 8A. An example of a perirectal or perianal incision (262) is illustrated at FIG. 8B. Another example of a perirectal or perianal incision (264) is illustrated at FIG. 8C. An example of a perineal incision (266) is illustrated at FIG. 8D. All of these types of incision allow access to pelvic floor tissue for implantation of one or two portions of a sling in contact with levator tissue (illustrated in shadow). FIGS. 8A, 8B, 8C and 8D also illustrate examples of frames 261 in various sizes and placement on implants, for stiffening a portion of an implant that becomes located near a rectum when placed in a patient.

Examples of various tissue paths, relevant anatomy, implant materials, features of implants (e.g., connectors, tensioning devices), insertion tools, are described, for example, in U.S. Publication Nos. 2002/0 I 61382 (Ser. No. 10/106,086) filed Mar. 25, 2002; 2005/0250977 (Ser. No. 10/840,646) filed May 7, 2004; and 2005/0245787 (Ser. No. 10/834,943) filed Apr. 30, 2004; 2005/0143618 (Ser. No. 11/064,875) filed Feb. 24, 2005; and U.S. Pat. No. 6,971,986 (Ser. No. 10/280,341) filed Oct. 25, 2002; U.S. Pat. No. 6,802,807 (Ser. No. 09/917,445) filed Jul. 27, 200 I; U.S. Pat. No. 6,612,977 (Ser. No. 09/917,443) filed Jul. 27, 2001; U.S. Pat. No. 6,911,003 (Ser. No. 10/377,101) filed Mar. 3, 2003; U.S. Pat. No. 7,070,556 (Ser. No. 10/306,179) filed Nov. 27, 2002; PCT/US2007/004015 "Surgical Articles and Methods for Treating Pelvic Conditions," filed Feb. 16, 2007; PCT/US2007/014120 "Surgical Implants, Tools, and Methods for Treating Pelvic Conditions," filed Jun. 15, 2007; WO 2008/013867 A1 "Surgical Articles and Methods for Treating Pelvic Conditions; and PCT/US07/016760, filed Jul. 25, 2007; the entireties of each of these being incorporated herein by reference.

Example Levator Distention Repair

The following general steps can be used for installing an implant as generally described. The specific steps and features of the implant are not limiting. For instance, the implant is described as including "anchors," but embodiments of the invention do not require anchors. For implants that include one or more features of a frame or a bearing for engaging a spreader, the basic steps of the method can be followed and modified to allow for optional steps such as folding or unfolding (or otherwise spreading) an implant, optionally using a spreader.

1. Blunt Dissection
   a. Make a transverse incision, approximately 2 cm inferior to the anus and 3 cm long, similar to a Krasky incision,
      i. There is an option here of dissecting through or superficial to the anococcygeal ligament. Dissection superficial to the ligament may provide a backstop for the rectum without putting it in tension or risking erosion. However, for severe fecal incontinence, or if greater tensioning was required, the ligament could be dissected as well and the mesh placed behind it.
   b. Insert a finger into the incision and tunnel toward the ischial spine on the patient left side. Use blunt dissection with your finger to open the space to the spine. The finger will lie between the levator muscle (medial) and fatty tissue (lateral).
   c. Make a sweeping motion with your finger, creating a space between the fat and muscle, between the ischial spine and the posterior edge of the obturator foramen on the inferior pubic ramus.
   d. Repeat B & C on the patient right side.
2. Mesh Placement with Needle
   a. Insert a needle through the anchor on one of the mesh arms.
   b. Placing your finger on the inferior pubic ramus near the obturator foramen, run the needle along your finger until the end with the anchor pushes into the tissue, into the obturator internus muscle.
   c. Remove the needle by pulling out of the incision. Give the mesh a tug to ensure the anchor has caught tissue. Insert the needle into the anchor on the other mesh arm.
   d. Place your finger on the ischial spine, and run the needle along your finger until the end with the anchor pushes into the tissue, near the ischial spine in the levator muscle.
   e. Remove the needle.
   f. Sweep along the mesh, smoothing the area between the anchors and sweeping the tail end beneath the rectum.
   g. Repeat steps A-F on the contralateral side.
3. Close incision with suture.
   a. If the ligament was dissected, rejoin the ends of the ligament over the mesh before closing the incision.

What is claimed is:

1. A method of supporting tissue of the pelvic region, the method comprising
   creating an incision that allows access to a pelvic region,
   providing a pelvic implant comprising a tissue support portion and an extension portion extending from the tissue support portion,
   providing a spreader tool comprising a handle, an elongate shaft having a distal end, a first jaw hingedly coupled to the elongate shaft at a connection location, a second jaw hingedly coupled to the elongate shaft, and a bias member operatively coupled to and extending between the first jaw and the second jaw, the bias member being disposed distally of the connection location,
   passing the implant through the incision and placing the tissue support portion to support tissue of the pelvic region,
   inserting the spreader through the incision to locate the spreader at a location of the implant, and
   using the spreader to spread material of the implant.

2. The method of claim 1 wherein the spreader comprises two jaws that can engage the implant and that can be selectively spread and unspread to spread or unspread the implant.

3. The method of claim 1 wherein the spreader comprises a hollow shaft, and the spreader can be extended from the shaft to take on a spread configuration, and retracted into the shaft to take on an unspread configuration.

4. The method of claim 1 comprising
   engaging the spreader and implant,
   placing the spreader in an unspread configuration and causing the implant to be placed in an unspread configuration,
   passing the spreader in its unspread configuration and the implant in its unspread configuration through the incision, and
   spreading the spreader to spread the implant.

5. The method of claim 1 comprising
   inserting the implant with an insertion tool and placing the implant at a position in the pelvic region,
   removing the insertion tool,
   inserting the spreader through an incision and engaging the spreader and implant while at the position in the pelvic region,
   spreading the spreader to spread the implant at the position in the pelvic region.

6. The method of claim 1 wherein the implant comprises a bearing for engaging a spreader.

7. A method according to claim 1 comprising placing the support portion inferior to a superficial transverse perineal muscle.

8. A method according to claim 1 comprising extending the extension portion to contact tissue of the pelvic region to cause the extension portion to support the tissue support portion and the tissue support portion to support levator tissue.

9. A method according to claim 1 comprising securing a distal end of the extension portion to periostium of a pubic bone in a region of an ischial tuberosity.

10. A method according to claim 1 comprising extending a portion of the implant through a tissue path between levator ani muscle and obturator internus muscle and attaching the extension portion at an arcus tendineus.

11. A kit comprising an implant and a spreader tool,
    the spreader tool comprising a handle, an elongate shaft having a distal end, and a spreader at the distal end of the shaft, the spreader including a first jaw hingedly coupled to the elongate shaft at a connection location, a second jaw hingedly coupled to the elongate shaft, and a bias member operatively coupled to and extending between the first jaw and to the second jaw, the bias member being located distally of the connection location,
    the implant comprising a tissue support portion and an extension portion.

12. The kit of claim 11 wherein the implant comprises a bearing for engaging the spreader.

13. A kit according to claim 11 comprising two bearings for engaging the spreader.

* * * * *